United States Patent
Sattlegger et al.

(10) Patent No.: US 6,653,508 B2
(45) Date of Patent: Nov. 25, 2003

(54) 3-AMINO-2-BENZYL-1-PHENYLPROPANE DERIVATIVES

(75) Inventors: Michael Sattlegger, Bonn (DE); Helmut Buschmann, Aachen (DE); Babette-Yvonne Koegel, Langerwehe-Hamich (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/046,567

(22) Filed: Jan. 16, 2002

(65) Prior Publication Data

US 2002/0161262 A1 Oct. 31, 2002

Related U.S. Application Data

(63) Continuation of application No. PCT/EP00/05820, filed on Jun. 23, 2000.

(30) Foreign Application Priority Data

Jul. 16, 1999 (DE) .......................................... 199 33 421

(51) Int. Cl.[7] .......................... C07C 225/00; A61K 31/13
(52) U.S. Cl. .......................... 564/342; 564/317; 564/355; 564/361; 564/363; 564/344; 564/345; 564/378; 564/383; 564/265; 514/644; 514/648; 514/653; 514/654
(58) Field of Search ............................... 564/317, 355, 564/361, 363, 342, 344, 345, 378, 383, 265, 445; 514/644, 648, 653, 654

(56) References Cited

U.S. PATENT DOCUMENTS

| | | | |
|---|---|---|---|
| 3,277,165 A | * | 10/1966 | Schultz |
| 3,342,829 A | * | 9/1967 | Schorr |
| 6,248,737 B1 | | 6/1995 | Buschmann et al. |
| 6,344,558 B1 | | 2/2002 | Buschmann et al. |

FOREIGN PATENT DOCUMENTS

| | | | |
|---|---|---|---|
| DE | 938732 A | * | 7/1961 |
| DE | 901438 A | * | 7/1962 |
| DE | 44 26 245 | | 7/1994 |
| GB | 901438 | | 4/1959 |
| GB | 938732 | | 11/1960 |
| GB | 938732 | * | 10/1963 |

| | | | |
|---|---|---|---|
| WO | WO 98/56752 | | 6/1998 |
| WO | 8856752 A | * | 12/1998 |

OTHER PUBLICATIONS

Cavalla J F et al: "Compounds Derived Form the Manniach Basis of Bet6ha–Phenyopropiopheone" Journal of Demdicianl Chemistryo, vol. 7, No. 6, pp. 716–721, Nov. 1, 1964.*
J.A. Gautier et al: Bulletin de la Societe Chimique de France, 1969, Seiten 4356–4361, XP002153391.*
W. H. Edgerton et al: Journal of the Americam Pharmaceutical Association., D. 48, 1859, Seiten 320–323, XP002153992, Seite 321; Beispiele 2–5,8,31; Tabelle I.*
XP–002062239 Cavalla et al., "Compounds Derived from the Mannich Bases of β–Phenylpropiophenone" *Journal of Medicinal Chemistry* (1961) 716–721.
XP–002153991 Gautier et al., "Reductions suivies de transformations dans la' ammmoniac liquide" *Bulletin de la Societe Chimique de France* (1969) 4356–4361.
XP–002153992 Edgerton et al., "Substituited α–Benzylphenethylamines" *American Pharmaceutical Association* (1959) 320–323.
Lespagnol et al. "Use of benzylacetophenone in the preparation of amino ketones of pharmacological interest" *Congr Sci. Pharm. Conf. Comun.* (1961) 660–669.
Lespagnol et al. "Phenylpropanolamines" *Bull. Soc. Chim. France* (1963) 2747–2748.
Lespagnol et al. "Comparison of the physiological actions of some derivatives of 1–amino 2–benzoyl–2–benzylethane and their iodomethylates" *Compt. Rend.* (1961) 808–9.
Bumgardner et al. "Elimination Reactions VII. 1–Benzyl–2–phenylcyclopropane and Olefins from 2–Benzyl–3–phenylpropyltrimethylammonium Iodide" *J. Am. Chem. Soc.* (1966) 5518–21.
Klusa et al. "Pharmacological Investigation of Amino Diketones" *Inst. Org. Sin.* (2000).
Raffa et al. "Complementary and Synergistic Antinociceptive Interaction between the Enentiomers of Tramadol" *J. Pharm. And Exp. Ther.* (1993) 331–340.

* cited by examiner

Primary Examiner—Samuel Barts
(74) Attorney, Agent, or Firm—Crowell & Moring LLP

(57) ABSTRACT

Substituted 3-amino-2-benzyl-1-phenlypropane derivatives, methods for preparing them, pharmaceutical compositions containing them, and methods of using them to treat various medical conditions.

61 Claims, No Drawings

3-AMINO-2-BENZYL-1-PHENYLPROPANE DERIVATIVES

CROSS REFERENCE TO RELATED APPLICATIONS

The present application is a continuation of international patent application no. PCT/EP00/05820, filed Jun. 23, 2000, designating the United States of America, the entire disclosure of which is incorporated herein by reference. Priority is claimed based on Federal Republic of Germany patent application no. DE 199 33 421.8, filed Jul. 16, 1999.

BACKGROUND OF THE INVENTION

The present invention relates to substituted 3-amino-2-benzyl-1-phenylpropane derivatives, processes for their preparation, pharmaceutical products containing these compounds, as well as the use of these substances for producing pharmaceutical products.

Pain is one of the main symptoms present in clinical practice, and there is a universal need for effective treatments for pain. The urgent need to provide a patient-oriented and targeted treatment for chronic and non-chronic painful conditions, which is understood to include the successful and satisfactory treatment of pain for patients, is documented in the large number of scientific articles that have recently been published in the field of applied analgesics and in basic research on pain relief. Thus, 1-phenyl-3-dimethylaminopropane compounds having an analgesic effect are known for example from DE-A-44 26 245.

Conventional opioids such as, e.g. morphine are effective in the treatment of severe to extremely severe pain. However, their undesirable side effects include, inter alia, respiratory depression, vomiting, sedation, constipation, as well as tolerance development. Also, they are less effective in neuropathic or incidental painful conditions such as frequently occur, especially in patients with tumours.

Tramadol hydrochloride-(1RS,2RS)-2-[(dimethylamino)methyl]-1-(3-methoxyphenyl)cyclohexanol occupies a special position among analgesics acting on the central nervous system, since this active substance has a powerful pain-inhibiting effect without the side effects known in the case of opioids (J. Pharmacol. Exptl. Ther. 267, 33 (1993)).

2-Benzyl-3-dimethylamino-1-phenylpropane and the corresponding methyl iodide are described in J. Am. Chem. Soc., 1966, 88, 5518–5521 as an intermediate product of a γ-elimination reaction. The analgesic effect of 1,3-diphenylpropanol derivatives and β-phenylpropiophenone derivatives is described in J. Med. Chem., 1964, 7, S 716–721 and Bull. Soc. Chim. Fr., 1963, 12, 2747–2748, though a detailed investigation has not been carried out however on account of undesirable side effects.

SUMMARY OF THE INVENTION

The object of the invention was accordingly to provide analgesically effective substances that are suitable for treating severe pain, in particular for treating chronic and neuropathic pain. Furthermore these active substances should exhibit as few as possible of the side effects of the opioid analgesics, such as for example nausea, vomiting, dependence, respiratory depression and constipation.

According to the invention this is achieved by substituted 3-amino-2-benzyl-1-phenylpropanes of the general formula I, these compounds having a pronounced analgesic effect.

The present invention accordingly provides substituted 3-amino-2-benzyl-1-phenylpropane derivatives of the general formula I,

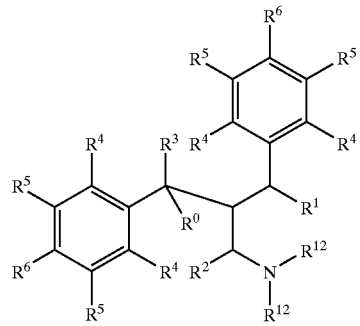

wherein
$R^0$ denotes H, OH or a single bond,
$R^1$ denotes H, a $C_{1-10}$-alkyl, an aryl or an aryl radical bound via a $C_{1-6}$-alkylene group, preferably denotes H, a $C_{1-3}$-alkyl or an aryl radical bound via a $C_{1-3}$-alkylene group,
$R^2$ denotes H, a $C_{1-10}$-alkyl, an aryl, or an aryl radical bound via a $C_{1-6}$-alkylene group, preferably denotes H, a $C_{1-3}$-alkyl or an aryl radical bound via a $C_{1-3}$-alkylene group,
$R^3$ denotes H, OH, $NH_2$, halogen, $OR^7$, $OHR^8$, $CHR^9$, a $C_{1-10}$-alkyl, a $C_{2-10}$-alkenyl, an aryl or an aryl radical bound via a $C_{1-6}$-alkylene group, and preferably denotes H, F, Cl, a $C_{1-3}$-alkyl, a $C_{2-3}$-alkenyl- or an aryl radical bound via a $C_{1-3}$-alkylene group,
or together with $R^0$ denotes a group =O, =$CHR^{11}$ or =N—OH, preferably =O,
$R^4$-radicals, which may be identical or different, denote H, OH, CN, $OR^7$, $SR^7$, halogen, a $C_{1-10}$-alkyl, a $PO(OR^{10})_3$, an aryl, a heterocyclyl, an aryl or heterocyclyl radical bound via a $C_{1-6}$ alkylene group, and preferably denote H, F, Cl, a $C_{1-6}$-alkyl, an aryl or heterocyclyl radical bound via a $C_{1-3}$-alkylene group,
$R^5$-radicals, which may be identical or different, denote H, OH, CN, $OR^7$, $SR^7$, halogen, a $C_{1-10}$-alkyl, a $PO(OR^{10})_3$, an aryl, a heterocyclyl, or an aryl or heterocyclyl radical bound via a $C_{1-6}$ alkylene group, and preferably denote H, F, Cl, a $C_{1-6}$-alkyl or an aryl or heterocyclyl radical bound via a $C_{1-3}$-alkylene group,
$R^6$-radicals, which may be identical or different, denote H, OH, CN, $OR^7$, $SR^7$, halogen, a $C_{1-10}$-alkyl, a $PO(OR^{10})_3$, an aryl, a heterocyclyl, or an aryl or heterocyclyl radical bound via a $C_{1-6}$ alkylene group, and preferably denote H, F, Cl, a $C_{1-6}$-alkyl or an aryl or heterocyclyl radical bound via a $C_{1-3}$-alkylene group,
$R^7$-radicals, which may be identical or different, denote a $C_{1-10}$-alkyl, an aryl or an aryl radical bound via a $C_{1-6}$ alkylene group, and preferably denote $C_{1-3}$-alkyl or an aryl radical bound via a $C_{1-3}$-alkylene group,
$R^8$ denotes a $C_{1-10}$-alkyl, an aryl or an aryl radical bound via a $C_{1-6}$-alkylene group, and preferably denotes a $C_{1-3}$-alkyl or an aryl radical bound via a $C_{1-3}$-alkylene group,
$R^9$ denotes OH, halogen, $OR^{10}$, $SR^{10}$ or a $C_{1-10}$-alkyl radical, and preferably denotes F, Cl or a $C_{1-3}$-alkyl radical,
$R^{10}$ denotes a $C_{1-10}$-alkyl or a $C_{4-8}$-cycloalkyl radical, preferably a $C_{1-3}$-alkyl radical,
$R^{11}$ denotes a $C_{1-10}$-alkyl radical, preferably a $C_{1-3}$-alkyl radical, $R^{12}$-radicals, which may be identical or different, denote H, a $C_{1-10}$-alkyl, a $C_{4-8}$-cycloalkyl, an aryl or an aryl radical bound via a $C_{1-6}$-alkylene group, preferably a $C_{1-3}$-alkyl radical, and/or their enantiomers, diastereomers, bases or salts of physiologically compatible acids, the compounds of the general formula I' being excluded

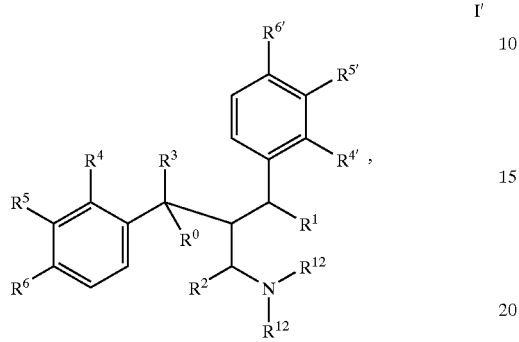

I' wherein the radicals are $R^0$ to $R^6$ and the radicals $R^{4'}$ to $R^{6'}$ denote H and also the radicals $R^{12}$ in each case denote $CH_3$, as well as the corresponding methyliodide, wherein the radicals $R^0$ and $R^3$ together denote the group =O and $R^1$, $R^2$, $R^4$ to $R^6$ and $R^{4'}$ to $R^{6'}$ denote H and also the radicals $R^{12}$ in each case denote $CH_3$, as well as the corresponding hydrochloride, wherein $R^0$ and $R^3$ together denote the group =O, $R^6$ denotes the group $OCH_3$ and $R^1$, $R^2$, $R^4$, $R^5$ and $R^{4'}$ to $R^{6'}$ denote H, and also the radicals $R^{12}$ in each case denote $CH^3$, as hydrochloride, wherein $R^0$ and $R^3$ together denote the group =O, $R^{6'}$ denotes the group $OCH_3$ and $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ and $R^3$ together denote the group =O, $R^{6'}$ denotes Cl and $R^1$, $R^2$, $R^4$ to $R^6$, $R^{4'}$ and $R^{5'}$ denote H, and also the radicals $R^{12}$ in each case denote $CH_3$, wherein $R^0$ and $R^3$ together denote the group =O, $R^{5'}$ and $R^{6'}$ in each case denote the group $OCH_3$, and $R^1$, $R^2$, $R^4$ to $R^6$ and $R^{4'}$ denote H, and also the radicals $R^{12}$ in each case denote $CH_3$, as hydrochloride, wherein $R^0$ and $R^3$ together denote the group =O, $R^4$, $R^6$ and $R^{6'}$ in each case denote the group $OCH_3$, and $R^1$, $R^2$, $R^5$, $R^{4'}$ and $R^{5'}$ denote H, and also the radicals $R^{12}$ in each case denote $CH_3$, as hydrochloride, wherein $R^0$ denotes OH, $R^3$ denotes H, $CH_3$, unbranched $C_3H_7$, unbranched $C_5H_{11}$, cyclohexyl, phenyl or benzyl, and $R^1$, $R^2$, $R^4$ to $R^6$ and $R^{4'}$ to $R^{6'}$ denote H, and also the radicals $R^{12}$ in each case denote $CH_3$, as well as the corresponding hydrochlorides, wherein $R^0$ denotes OH, $R^3$ denotes $C_2H_5$ and $R^1$, $R^2$, $R^4$ to $R^6$ and $R^{4'}$ to $R^{6'}$ denote H and also the radicals $R^{12}$ n each case denote $CH_3$, as well as the corresponding hydrochloride and the corresponding methyliodide, wherein $R^0$ denotes OH, $R^3$ denotes phenyl, $R^6$ denotes Cl, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes Cl, $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ denotes OH, $R^3$ denotes phenyl, $R^{5'}$, $R^{6'}$ in each case denote the group $OCH_3$, $R^1$, $R^2$, $R^4$ to $R^6$ and $R^{4'}$ denote H, and also the radicals $R^{12}$ in each case denote $CH_3$, as hydrochloride, wherein $R^0$ denotes OH, $R^3$ denotes phenyl, $R^6$ denotes the group $OCH_3$, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes the group $OCH_3$, $R^1$, $R^2$, $R^4$ to $R^6$, $R^{4'}$ and $R^{5'}$ denote H, and also the radicals $R^{12}$ in each case denote $CH_3$, as well as the corresponding hydrochloride and the corresponding methyliodide, wherein $R^0$ denotes OH, $R^3$ denotes phenyl, $R^6$ and $R^{6'}$ in each case denote the group $OCH_3$, $R^1$, $R^2$, $R^4$, $R^5$, $R^{4'}$ and $R^{5'}$ denote H, and also the radicals $R^{12}$ in each case denote $CH_3$, as well as the corresponding hydrochloride, wherein $R^0$ denotes OH, $R^{6'}$ denotes $OCH_3$, $R^1$ to $R^6$, $R^{4'}$ and $R^{5'}$ denote H, and also the radicals $R^{12}$ in each case denote $CH_3$, as well as the corresponding hydrochloride, wherein $R^0$, $R^1$, $R^2$, the radicals $R^4$ to $R^6$, the radicals $R^{4'}$ to $R^{6'}$ in each case denote H, the radical $R^3$ denotes phenyl, and also the radicals $R^{12}$ in each case denote $CH_3$, as well as the corresponding hydrochloride, wherein $R^1$, $R^2$, the radicals $R^4$ to $R^6$ the radicals $R^{4'}$ to $R^{6'}$ in each case denote H, the radicals $R^3$ and $R^0$ together denote the group =$CHR^{11}$, and also the radical $R^{11}$ and in each case the radicals $R^{12}$ denote $CH_3$, as hydrochloride wherein $R^1$, $R^2$, the radicals $R^4$ to $R^6$, the radicals $R^{4'}$ to $R^{6'}$ in each case denote H, the radicals $R^3$ and $R^0$ together denote the group =N—OH, and also the radicals $R^{12}$ in each case denote $CH_3$, as well as the corresponding hydrochloride, and wherein $R^1$, $R^2$, the radicals $R^4$ to $R^6$, the radicals $R^{4'}$ to $R^{6'}$ in each case denote H, the radicals $R^3$ and $R^0$ together denote the group =O, and also the radicals $R^{12}$ in each case denote $C_2H_5$, as hydrochloride.

The term alkyl radicals is also understood to mean hydrocarbons substituted at least once, preferably by halogen, particularly preferably by fluorine. If these hydrocarbons contain more than one substituent, then the latter may be identical or different. The alkyl radicals are preferably methyl, ethyl, propyl, 1-methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, heptyl, nonyl or decanyl.

The term alkenyl radicals is also understood to mean hydrocarbons substituted at least once, preferably by halogen, particularly preferably by fluorine, and that contain at least one double bond. If the alkenyl radical contains more than one substituent, then the latter may be identical or different. The alkenyl radicals are preferably 2-propenyl, 2-butenyl, 1-methyl-2-propenyl or 2-methyl-2-propenyl.

The term aryl radical is also understood to mean phenyl or naphthyl radicals substituted at least once by an OH, a halogen, preferably F and/or Cl, a $CF_3$, a $C_{1-6}$ alkyl, a $C_{1-6}$ alkoxy, a $C_{1-7}$ cycloalkoxy, a $C_{3-7}$ cycloalkyl, a $C_{2-6}$ alkylene or phenyl radical. The phenyl radicals may also be condensed with further rings.

The term heterocyclyl radical is also understood to mean saturated as well as unsaturated heterocyclic compounds, preferably 5–7-membered heterocyclic compounds, that contain at least one heteroatom, preferably nitrogen, oxygen and/or sulfur, particularly preferably nitrogen and/or oxygen. The saturated heterocyclic compounds are preferably 1,4-dioxane, tetrohydrofuran or 1,4 thioxane. The unsaturated heterocyclic compounds are preferably furan, thiophene, pyridine, pyrimidine, thiazole, oxazole, isoxazole, pyridazine, pyrazine, quinoline, isoquinoline, phthalazine or quinazoline.

Particularly preferred are the following substituted 2-benzyl-3-dimethylamino-1-phenylpropane derivatives:

(E)-(2RS)-(3RS)-3-benzyl-4-dimethylamino-2-(3-methoxyphenyl)-butan-2-ol or the corresponding hydrochloride (2RS)-3-[1-(1-benzyl-2-dimethylaminoethyl)-vinyl]-phenol or the corresponding hydrochloride (2RS)-1-(3-benzyloxyphenyl)-2-dimethylaminomethyl-3-phenylpropan-1-one or the corresponding hydrochloride E-(2RS)-(3RS)-2-benzyl-1-dimethylamino-3-(3-methoxyphenyl)-pentan-3-ol or the corresponding hydrochloride (3RS)-2-benzyl-1-(4-chlorophenyl)-3-dimethylaminopropan-1-one or the corresponding hydrochloride E-(2RS)-(3RS)-2-benzyl-3-(3-benzyloxyphenyl)-1-dimethylaminopentan-3-ol or the corresponding hydrochloride E-(2RS)-(3RS)-3-(2-benzyl-3-dimethylamino-1-hydroxypropyl)-phenol or the corresponding hydrochloride E-(2RS)-(4RS)-3-benzyl-2-(3-benzyloxyphenyl)-4-dimethylaminobutan-2-ol or the corresponding hydrochloride E-(2RS)-(3RS)-3-(2-benzyl-3-dimethylamino-1-methyl-1-hydroxypropyl)-phenol or the corresponding hydrochloride E-(2RS)-(3RS)-3-(2-benzyl-3-dimethylamino-1-ethyl-1-hydroxypropyl)-phenol or the corresponding hydrochloride (Z/E)-(2RS)-3-(1-(1-benzyl-3-dimethylaminoethyl)-propenyl]-phenol or the corresponding hydrochloride (2RS)-3-dimethylamino-2-(4-methoxybenzyl)-1-(3-methoxyphenyl)-propan-1-one or the corresponding hydrochloride Z-(1RS)-(2RS)-2-benzyl-1-(4-chlorophenyl)-3-dimethylamino-1-(3-methoxyphenyl)-propan-1-ol or the corresponding hydrochloride E-(2RS)-(3RS)-2-benzyl-3-(4-chlorophenyl)-1-dimethylaminopentan-3-ol or the corresponding hydrochloride E-(2RS)-(3RS)-3-benzyl-2-(4-chlorophenyl)-4-dimethylamino-1-phenylbutan-2-ol or the corresponding hydrochloride Z-(2RS)-(3RS)-3-benzyl-2-(4-chlorophenyl)-4-dimethylamino-1-phenylbutan-2-ol or the corresponding hydrochloride E-(2RS)-(3RS)-2-benzyl-3-dimethylamino-1,1-bis-(3-methoxyphenyl)-propan-1-ol or the corresponding hydrochloride E-(2RS)-(3RS)-2-dimethylaminomethyl-3-(3-methoxyphenyl)-1-phenylhexen-5-ol or the corresponding hydrochloride (2RS)-2-benzyl-3-dimethylamino-1-(3-trifluoromethylphenyl)-propan-1-one or the corresponding hydrochloride (2RS)-2-benzyl-3-dimethylamino-1-(3-hydroxyphenyl)-propan-1-one or the corresponding hydrochloride (2RS)-2-benzyl-1-(3,5-dimethoxyphenyl)-3-dimethylaminopropan-1-one or the corresponding hydrochloride (2RS)-2-benzyl-1-(2,5-dimethoxyphenyl)-3-dimethylaminopropan-1-one or the corresponding hydrochloride (1RS)-(2RS)-2-benzyl-1-(3-methoxyphenyl)-N,N-dimethylpropan-1,3-diamine or the corresponding hydrochloride (2RS)-2-benzyl-1-(2,3-dimethoxyphenyl)-3-dimethylaminopropan-1-one or the corresponding hydrochloride (+)-(R)-2-benzyl-3-dimethylamino-1-(3-methoxyphenyl)-propan-1-one or the corresponding hydrochloride (−)-(S)-2-benzyl-3-dimethylamino-1-(3-methoxyphenyl)-propan-1-one or the corresponding hydrochloride (2RS)-2-benzyl-1-(2,3-dichlorophenyl)-3-dimethylaminopropan-1-one or the corresponding hydrochloride (2RS)-2-benzyl-1-(2,5-dichlorophenyl)-3-dimethylaminopropan-1-one or the corresponding hydrochloride (2RS)-2-benzyl-3-dimethylamino-1-(2,3,4-trimethoxyphenyl)-propan-1-one or the corresponding hydrochloride (2RS)-2-benzyl-3-dimethylamino-1-(3,4,5-trimethoxyphenyl)-propan-1-one or the corresponding hydrochloride Z-(2RS)-[2-benzyl-3-(3-methoxyphenyl)-pent-3-enyl]-dimethylamine or the corresponding hydrochloride (2RS)-2-benzyl-1-(2,5-dihydroxyphenyl)-3-dimethylaminopropan-1-one or the corresponding hydrochloride E-(2RS)-(3RS)-2-dimethylaminomethyl-3-(3-methoxyphenyl)-1,3-diphenylpropan-1-one or the corresponding hydrochloride (2RS)-2-benzyl-3-dimethylamino-1-(2-methoxyphenyl)-propan-1-one or the corresponding hydrochloride (2RS)-2-benzyl-3-dimethylamino-1-naphthalen-2-yl-propan-1-one or the corresponding hydrochloride (2RS)-2-benzyl-3-dimethylamino-1-phenanthren-3-yl-propan-1-one or the corresponding hydrochloride (2RS)-2-benzyl-3-dimethylamino-1-(2-hydroxyphenyl)-propan-1-one or the corresponding hydrochloride (2RS)-2-benzyl-3-dimethylamino-1-(2-fluorophenyl)-propan-1-one or the corresponding hydrochloride (2RS)-2-benzyl-3-dimethylamino-1-(3-methylsulfanylphenyl)-propan-1-one or the corresponding hydrochloride E-(2RS)-(3RS)-[2-benzyl-3-(3-methoxyphenyl)-pentyl]-dimethylamine or the corresponding hydrochloride (Z/E)-(2RS)-(3RS)-[2-benzyl-3-(3-methoxyphenyl)-pentyl]-dimethylamine or the corresponding hydrochloride (2RS)-2-benzyl-3-dimethylamino-1-(2-hydroxy-5-methoxyphenyl)-propan-1-one or the corresponding hydrochloride (2RS)-3-(2-benzyl-3-dimethylaminopropionyl)-benzonitrile or the corresponding hydrochloride (2RS)-(3RS)-2-dimethylaminomethyl-1,3,3-tris-(3-methoxyphenyl)-propan-1-one or the corresponding hydrochloride (2RS)-2-benzyl-1-biphenyl-3-yl-3-dimethylaminopropan-1-one or the corresponding hydrochloride (2RS)-2-benzyl-3-dimethylamino-1-(6-methoxynaphthalen-2-yl)-1-one or the corresponding hydrochloride (2RS)-(3RS)-2-dimethylaminomethyl-1,3-bis-(3-methoxyphenyl)-3-phenylpropan-1-one or the corresponding hydrochloride Z-(2RS)-(3RS)-2-dimethylaminomethyl-1-(3-methoxyphenyl)-3,4-diphenylbutan-1-one or the corresponding hydrochloride (2RS)-2-benzyl-3-dimethylamino-1-(6-hydroxynaphthalen-2-yl)-propan-1-one or the corresponding hydrochloride (2RS)-(3RS)-3-(2-benzyl-3-dimethylamino-1-ethylpropyl)-phenol or the corresponding hydrochloride (2RS)-2-benzyl-1-biphenyl-2-yl-3-dimethylaminopropan-1-one or the corresponding hydrochloride (2RS)-(3RS)-2-dimethylaminomethyl-1-(3-methoxyphenyl)-3-phenylpentan-1-one or the corresponding hydrochloride (2RS)-2-benzyl-1-(2-chloro-4-fluorophenyl)-3-dimethylamino-propan-1-one or the corresponding hydrochloride (2RS)-2-dimethylaminomethyl-1-[(1RS)-3-(1-hydroxy-3-phenylpropyl)-phenyl]-3-phenylpropan-1-one or the corresponding hydrochloride (2RS)-3-dimethylamino-2-(2-fluorobenzyl)-1-(3-methoxyphenyl)-propan-1-one or the corresponding hydrochloride (2RS)-3-dimethylamino-2-(3-fluorobenzyl)-1-(3-methoxyphenyl)-propan-1-one or the corresponding hydrochloride (2RS)-3-dimethylamino-2-(4-fluorobenzyl)-1-(3-methoxyphenyl)-propan-1-one or the corresponding hydrochloride (2RS)-(3RS)-2-dimethylaminomethyl-3,3-bis-(3-methoxyphenyl)-1-naphthalen-2-yl-propan-1-one or the corresponding hydrochloride (2RS)-2-benzyl-3-dimethylamino-1-(3-methoxyphenyl)-propan-1-one or the corresponding hydrochloride Z-(2RS)-(3RS)-2-dimethylaminomethyl-1,3-diphenylpentan-1-one or the corresponding hydrochloride (2RS)-(3RS)-2-dimethylaminomethyl-1,3-diphenyl-3-p-tolylpropan-1-one or the corresponding hydrochloride (2RS)-(3RS)-2-dimethylaminomethyl-1,3,6-triphenylhexan-1-one or the corresponding hydrochloride E-(2RS)-(3RS)-3-benzyl-4-dimethylamino-2-(3-methoxyphenyl)-1-phenylbutan-2-ol or the corresponding hydrochloride (2RS)-(3RS)-3-benzyl-4-dimethylamino-1,1,1-trifluoro-2-(3-methoxyphenyl)-butan-2-ol E-(2RS)-[2-benzyl-3-(3-methoxyphenyl)-pent-3-enyl]-dimethylamine or the corresponding hydrochloride (+)-(R)-2-benzyl-3-dimethylamino-1-(3-hydroxyphenyl)-propan-1-one or the corresponding hydrochloride (2RS)-3-dimethylamino-2-(3-methylbenzyl)-1-(3-methoxyphenyl)-propan-1-one or the corresponding hydrochloride (−)-(S)-2-benzyl-3-dimethylamino-1-(3-hydroxyphenyl)-propan-1-one or the corresponding hydrochloride (2RS)-2-dimethylamino-2-(3-fluorobenzyl)-1-(3-hydroxyphenyl)-propan-1-one or the corresponding hydrochloride (2RS)-3-dimethylamino-2-(3-methoxybenzyl)-1-(3-methoxyphenyl)-propan-1-one or the corresponding hydrochloride (2RS)-2-benzyl-3-dimethylamino-1-(4-methoxy-2,3-dimethylphenyl)-propan-1-one or the corresponding hydrochloride (2RS)-2-(3-chlorobenzyl)-3-dimethylamino-1-(3-methoxyphenyl)-propan-1-one or the corresponding hydrochloride (2RS)-3-dimethylamino-1-(3-methoxyphenyl)-2-(3-methylbenzyl)-propan-1-one or the corresponding hydrochloride (2RS)-2-benzyl-3-dimethylamino-1-(2,4,6-trimethylphenyl)-propan-1-one or the corresponding hydrochloride (S)-(−)-3-dimethylamino-1-(3-methoxyphenyl)-2-(3-fluorobenzyl)-propan-1-one or the corresponding hydrochloride (R)-(+)-3-dimethylamino-1-(3-methoxyphenyl)-2-(3-fluorobenzyl)-propan-1-one or the corresponding hydrochloride (RS)-3-dimethylamino-1-(3-hydroxyphenyl)-2-(3methylbenzyl)-propan-1-one or the corresponding hydrochloride (RS)-2-benzyl-1-(2,4-dichlorophenyl)-3-dimethylaminopropan-1-one or the corresponding hydrochloride (RS)-3-dimethylamino-2-(4-flurobenzyl)-1-(3-hydroxyphenyl)-propan-1-one or the corresponding hydrochloride (RS)-1-(3-methoxyphenyl)-2-methylaminomethyl-3-m-tolylpropan-1-one or the corresponding hydrochloride (RS)-2-(3-chlorobenzyl)-3-dimethylamino-1-(3-hydroxyphenyl)-propan-1-one or the corresponding hydrochloride (RS)-3-(3,4-difluorophenyl)-2-dimethylaminomethyl-1-(3-methoxyphenyl)-propan-1-one or the corresponding hydrochloride (RS)-3-(3-fluorophenyl)-1-(3-methoxyphenyl)-2-methylaminomethyl-1-propan-1-one or the corresponding hydrochloride (RS)-3-(3-fluorophenyl)-1-(3-hydroxyphenyl)-2-methylaminomethyl-1-propan-1-one or the corresponding hydrochloride (RS)-1-(2,3-dihydrobenzo[1,4]dioxin-6-yl)-2-dimethylamino-methyl-3-phenylpropan-1-one or the corresponding hydrochloride (RS)-2-dimethylaminomethyl-1-(3-phenoxyphenyl)-3-phenylpropan-1-one or the corresponding hydrochloride (RS)-3-(3,4-difluorophenyl)-2-dimethylaminomethyl-1-(3-hydroxyphenyl)-propan-1-one or the corresponding hydrochloride (RS)-2-dimethylaminomethyl-1-(3-methoxyphenyl)-3-(3-trifluoromethylphenyl)propan-1-one or the corresponding hydrochloride (RS)-2-dimethylaminomethyl-1-(3-hydroxyphenyl)-3-(3-trifluoromethylphenyl)propan-1-one or the corresponding hydrochloride Z/E-(2RS)(3RS)-1-(4-chlorophenyl)-3-dimethylaminomethyl-2-(3-methoxyphenyl)-4-phenylbutan-2-ol or the corresponding hydrochloride Z/E-(2RS)(3RS)-1-(3-chlorophenyl)-3-dimethylaminomethyl-2-(3-methoxyphenyl)-4-phenylbutan-2-ol or the corresponding hydrochloride Z/E-(2RS)(3RS)-1-(2-chlorophenyl)-3-dimethylaminomethyl-2-(3-methoxyphenyl)-4-phenylbutan-2-ol or the corresponding hydrochloride The invention also provides processes for preparing substituted 3-amino-2-benzyl-1-phenylpropane derivatives of the general formula I, in which $R^0$ and $R^3$ together denote a group =O and $R^1$ denotes H, $R^2$ and $R^4$ to $R^6$ as well as $R^{12}$ have the meanings specified in the general formula I, which processes are characterised in that substituted aldehydes of the general formula II

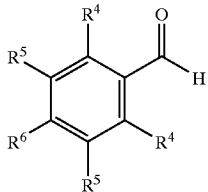

II are reacted in the presence of a magnesium in a Grignard reaction with compounds of the general formula III

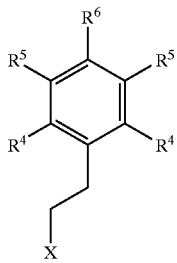

wherein X denotes Br, Cl or I, preferably Br, to form compounds of the general formula IV

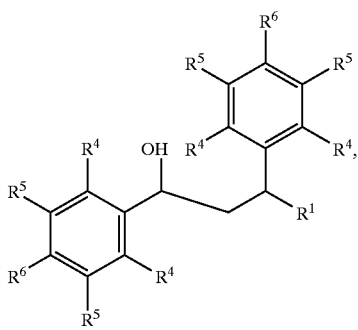

IV and are purified and isolated by conventional methods.

The compounds of the general formula IV are oxidised in solution, preferably in aqueous or ethereal solution, with an oxidising agent, preferably with inorganic salts, particularly preferably with potassium dichromate or sodium hydrochlorite to form compounds of the general formula V

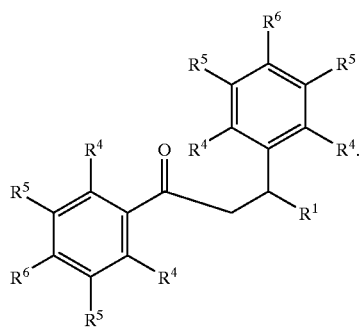

V

The compounds of the general formula V are then reacted with an iminium salt of an aldehyde and a compound of the general formula $NH(R^{12})_2 \cdot HCl$, wherein $R^{12}$ has the meaning according to the general formula I, in a Mannich reaction to form compounds of the general formula VI

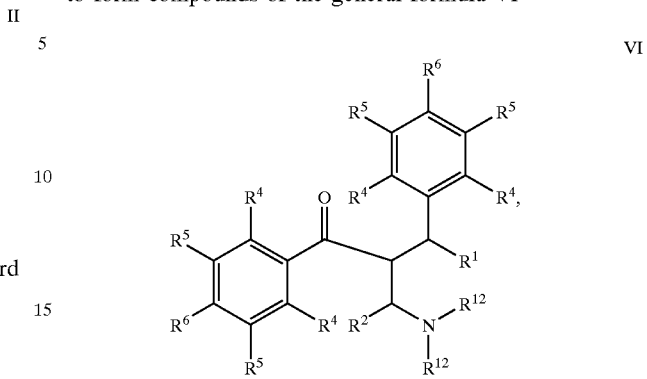

VI and are purified by conventional methods and are isolated as salts of physiologically compatible acids.

The invention furthermore provides processes for preparing substituted 3-amino-2-benzyl-1-phenylpropane derivatives of the general formula I, wherein $R^0$ denotes OH and $R^1$ denotes H, and $R^2$ to $R^6$ as well as $R^{12}$ have the meanings specified in the general formula I, which processes are characterised in that compounds of the general formula VI are reacted with an organometallic compound of the general formula $R^3MX$, wherein M denotes Li, Mg or Zn and X denotes Cl, Br or I, to form compounds of the general formula VII

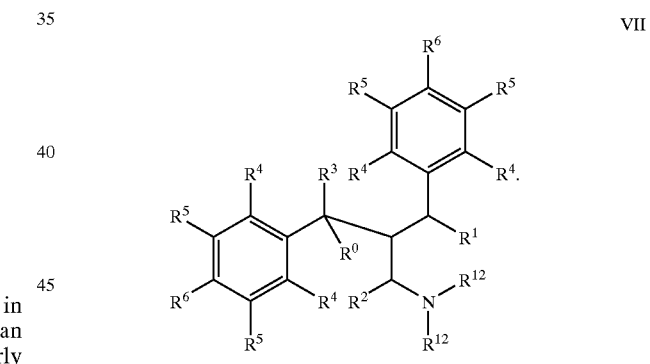

VII

In the reaction of a β-dimethylaminoketone of the general formula VI with an organometallic compound of the general formula $R^3MX$, tertiary alcohols of the general formula VII are preferably obtained having a configuration in which the amino group is arranged in the cis, threo (or Z, E) position to the hydroxyl group. The resulting tertiary alcohols of the general formula VII can be obtained in a diastereomer pure form by column chromatography separation or by crystallisation of their salts, preferably of the hydrochlorides.

The invention furthermore provides processes for preparing substituted 3-amino-2-benzyl-1-phenylpropane derivatives of the general formula I, wherein $R^0$ and $R^3$ together denote a group $=CHR^{11}$ and $R^1$ denotes H, and $R^2$ and $R^4$ to $R^6$ as well as $R^{12}$ have the meanings specified in the general formula I, which processes are characterised in that compounds of the general formula VII are treated with hydrogen bromide and the corresponding olefins of the general formula VIII

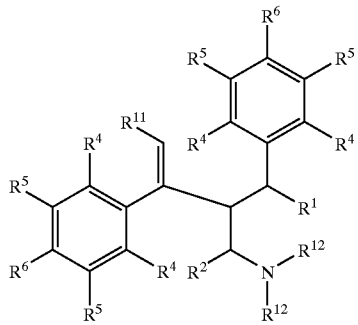

are isolated as salts of physiologically compatible acids.

The invention further provides processes for preparing substituted 3-amino-2-benzyl-1-phenylpropane compounds of formula I, wherein $R^0$ denotes H and $R^1$ denotes H, and $R^2$ to $R^6$ and also $R^{12}$ have the meanings specified in formula I, which processes are characterised in that compounds of formula VIII are hydrogenated ion the presence of a palladium/carbon catalyst with hydrogen to form corresponding alkanes of formula IX

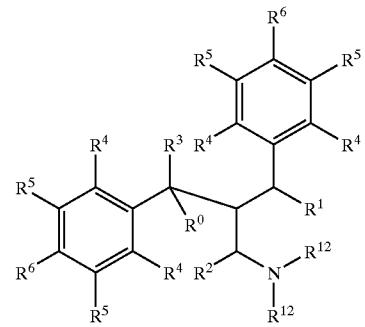

and the latter are isolated as salts of physiologically compatible acids.

The invention further provides processes for preparing substituted 3-amino-2-benzyl-1-phenylpropane derivatives of the general formula I, wherein $R^0$ and $R^3$ together denote a group =O and $R^1 \neq H$, and $R^2$ as well as $R^4$ to $R^6$ have the meanings specified in the general formula I, which processes are characterised in that substituted acetaldehydes of the general formula X

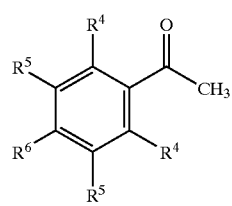

are reacted with substituted benzaldehydes of the general formula XI

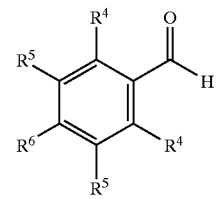

in an aldol condensation to form substituted 1,3-diphenylpropenones of the general formula XII

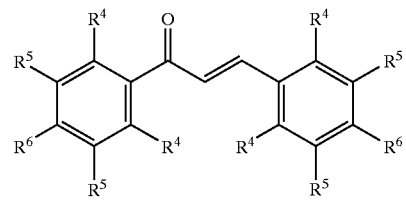

which are purified and isolated by conventional methods.

These compounds of formula XII are reacted with compounds that had been converted from compounds of the formula $R^1Br$ with magnesium into a Grignard compound and then by a transmetallisation with copper(1) iodide into the corresponding cuprates to form an enolate, and the enolate is then reacted in situ with the iminium salt of an aldehyde and a compound of the general formula $NH(R^{12})_2$·HCl, wherein $R^{12}$ has the meaning according to the general formula I. The resulting compounds of formula XIII

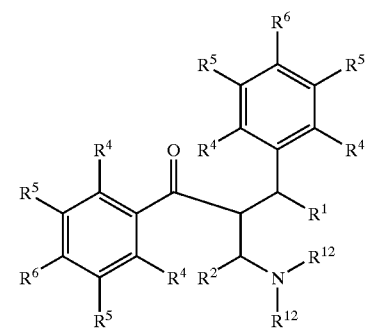

are purified by conventional methods and are isolated as salts of physiologically compatible acids.

The invention furthermore provides processes for preparing substituted 3-amino-2-benzyl-1-phenylpropane compounds of formula I, wherein $R^0$ denotes OH and $R^1 \neq H$, and $R^2$ to $R^6$ as well as $R^{12}$ have the meanings specified for formula I, which processes are characterised in that compounds of formula XIII are reacted with compounds of the formula $R^3MX$, wherein M denotes Li, Mg or Zn and X denotes Cl, Br or I, and the resulting compounds of formula XIV

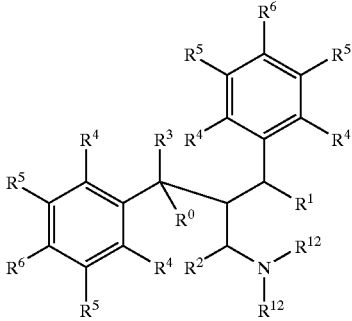

are purified by conventional methods and are isolated as salts of physiologically compatible acids.

The invention also provides processes for preparing substituted 3-amino-2-benzyl-1-phenylpropane compounds of formula I, wherein $R^0$ and $R^3$ together denote a group $=CHR^{11}$ and $R^1 \neq H$, and $R^2$ and $R^4$ to $R^6$ as well as $R^{12}$ have the meanings specified for formula I, wherein compounds of formula XIV are treated with hydrogen bromide to obtain corresponding olefins of formula XV

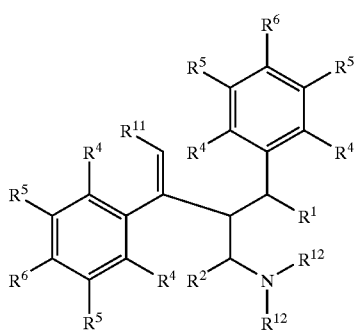

and the resulting olefins are purified by conventional methods and are isolated as salts of physiologically compatible acids.

The invention also provides processes for preparing substituted 3-amino-2-benzyl-1-phenylpropane compounds of formula I, wherein $R^0$ denotes H and $R^1 \neq H$, and $R^2$ to $R^6$ as well as $R^{12}$ have the meanings specified for formula I, wherein compounds of formula XV are hydrogenated with hydrogen in the presence of a palladium/carbon catalyst to form the corresponding alkanes of formula XVI

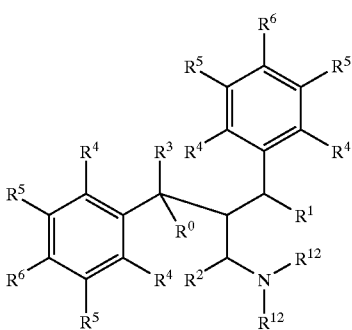

and the latter are purified by conventional methods and isolated as salts of physiologically compatible acids.

The invention furthermore provides processes for preparing compounds of formula I, wherein $R^4$ and/or $R^5$ and/or $R^6$ denote an OH group and $R^0$ to $R^3$ as well as $R^{12}$ have the meanings specified for formula I, wherein compounds of formula I, wherein $R^4$ and/or $R^5$ and/or $R^6$ denote a methoxy group and $R^0$ to $R^3$ as well as $R^{12}$ have the meanings specified for formula I, are treated with methionine in methanesulfonic acid, in particular at a temperature $\geq 60°$ C. (J. C. S. Perkin I 1977, 2288–2289).

The compounds of formula I can be converted in a known manner into their salts by reaction with physiologically compatible acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formation is preferably carried out in a solvent, for example diethyl ether, diisopropyl ether, alkyl acetates, acetone and/or 2-butanone. Moreover, trimethylchlorosilane in methyl ethyl ketone is suitable for preparing the hydrochlorides.

The substituted 3-amino-2-benzyl-1-phenylpropane compounds of formula I according to the invention are toxicologically safe and accordingly represent suitable pharmaceutical active constituents.

The invention furthermore provides pharmaceutical products that contain as active substance at least one substituted 3-amino-2-benzyl-1-phenylpropane derivative of the general formula I and/or their enantiomers, diastereomers, bases or salts of physiologically compatible acids and optionally further active constituents and/or auxiliaries. Excluded are compounds of the general formula I' wherein the radicals $R^0$ and $R^3$ together denote the group $=O$ and R, $R^2$, $R^4$ to $R^6$ and $R^{4'}$ to $R^{6'}$ denote H and also the radicals $R^{12}$ in each case denote $CH_3$, as well as the corresponding hydrochloride, wherein $R^0$ and $R^3$ together denote the group $=O$, $R^6$ denotes the group $OCH_3$, and $R^1$, $R^2$, $R^4$, $R^5$ and $R^{4'}$ to $R^{6'}$ denote H and also the radicals $R^{12}$ in each case denote $CH_3$, as hydrochloride, wherein $R^0$ and $R^3$ together denote the group $=O$, $R^{6'}$ denotes the group $OCH_3$, and $R^1$, $R^2$, $R^4$ to $R^6$, $R^{4'}$ and $R^{5'}$ denote H and also the radicals $R^{12}$ in each case denote $CH_3$, as well as the corresponding hydrochloride, wherein $R^0$ and $R^3$ together denote the group $=O$, $R^{6'}$ denotes Cl, and $R^1$, $R^2$, $R^4$ to $R^6$, $R^{4'}$ and $R^{5'}$ denote H, and also the radicals $R^{12}$ in each case denote $CH_3$, wherein $R^0$ and $R^3$ together denote the group $=O$, $R^{5'}$ and $R^{6'}$ in each case denote the group $OCH_3$, and $R^1$, $R^2$, $R^4$ to $R^6$ and $R^{4'}$ denote H, and also the radicals $R^{12}$ in each case denote $CH_3$, as hydrochloride, wherein $R^0$ and $R^3$ together denote the group $=O$, $R^4$, $R^6$ and $R^{6'}$ in each case denote the group $OCH_3$, and $R^1$, $R^2$, $R^5$, $R^{4'}$ and $R^{5'}$ denote H and also the radicals $R^{12}$ in each case denote $CH_3$, as hydrochloride, wherein $R^0$ denotes OH, $R^3$ denotes H, $CH_3$, unbranched $C_3H_7$, unbranched $C_5H_{11}$, cyclohexyl, phenyl or benzyl, and $R^1$, $R^2$, $R^4$ to $R^6$ and $R^{4'}$ to $R^{6'}$ denote H and also the radicals $R^{12}$ in each case denote $CH_3$, as well as the corresponding hydrochlorides, wherein $R^0$ denotes OH, $R^3$ denotes $C_2H_5$, and $R^1$, $R^2$, $R^4$ to $R^6$ and $R^{4'}$ to $R^{6'}$ denote H and also the radicals $R^{12}$ in each case denote $CH_3$, as well as the corresponding hydrochloride and the corresponding methyliodide, wherein $R^0$ denotes OH, $R^3$ denotes phenyl, $R^6$ denotes Cl, $R^1$, $R^2$, $R^4$, $R^5$ and $R^{4'}$ to $R^{6'}$ denote H and also the radicals $R^{12}$ in each case denote $CH_3$, as well as the corresponding hydrochloride, wherein $R^0$ denotes OH, $R^3$ denotes phenyl, $R^{6'}$ denotes Cl, $R^1$, $R^2$, $R^4$ to $R^6$, $R^{4'}$ and $R^{5'}$ denote H and also the radicals $R^{12}$ in each case denote $CH_3$, as well as the corresponding hydrochloride, wherein $R^0$ denotes OH, $R^3$ denotes phenyl, $R^{5'}$, $R^{6'}$ in each case denote the group $OCH_3$, $R^1$, $R^2$, $R^4$ to $R^6$ and $R^{4'}$ denote H, and also the radicals $R^{12}$ in each case denote $CH_3$, as hydrochloride, wherein $R^0$ denotes OH, $R^3$ denotes phenyl, $R^6$ denotes the group $OCH_3$, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes the group $OCH_3$, $R^1$, $R^2$, $R^4$ to $R^{6'}$ $R^{4'}$ and $R^{5'}$ denote H, and also the radicals $R^{12}$ in each case denote $CH_3$, as well as the corresponding hydrochloride and the corresponding methyliodide, wherein $R^0$ denotes OH, $R^3$ denotes phenyl, $R^6$ and $R^{6'}$ in each case denote the group $OCH_3$, $R^1$, $R^2$, $R^4$, $R^5$, $R^{4'}$ and $R^{5'}$ denote H, and also the radicals $R^{12}$ in each case denote $CH_3$, as well as the corresponding hydrochloride, wherein $R^0$ denotes OH, $R^{6'}$ denotes $OCH_3$, $R^1$ to $R^6$, $R^{4'}$ and $R^{5'}$ denote H, and also the radicals $R^{12}$ in each case denote $CH_3$, as well as the corresponding hydrochloride, wherein $R^0$, $R^1$, $R^2$, the radicals $R^4$ to $R^6$, the radicals $R^{4'}$ to $R^{6'}$ in each case denote H, the radical $R^3$ denotes phenyl, and also the radicals $R^{12}$ in each case denote $CH_3$, as well as the corresponding hydrochloride, wherein $R^1$, $R^2$, the radicals $R^4$ to $R^6$, the radicals $R^{4'}$ to $R^{6'}$ in each case denote H, the radicals $R^3$ and $R^0$ together denote the group $=CHR^{11}$ and also the radical $R^{11}$ and in each the radicals $R^{12}$ denote $CH_3$, as hydrochloride, and wherein $R^1$, $R^2$, the radicals $R^4$ to $R^6$, the radicals $R^{4'}$ to $R^{6'}$ in each case denote H, the radicals $R^3$ and $R^0$ together denote the group $=N—OH$ and also the radicals $R^{12}$ in each case denote $CH_3$, as well as the corresponding hydrochloride.

The invention further provides for the use of at least one substituted 3-amino-2-benzyl-1-phenylpropane derivative of the general formula I and/or their enantiomers, diastereomers, bases or salts of physiologically compatible acids for preparing a pharmaceutical product for treating pain, the compounds of the general formula I' being excluded, wherein the radicals $R^0$ and $R^3$ together denote the group $=O$ and $R^1$, $R^2$, $R^4$ to $R^6$ and $R^{4'}$ to 6, denote H and also the radicals $R^{12}$ in each case denote $CH_3$, as well as the corresponding hydrochloride, wherein $R^0$ and $R^3$ together denote the group $=O$, $R^6$ denotes the group $OCH_3$ and $R^1$, $R^2$, $R^4$, $R^5$ and $R^{4'}$ to $R^{6'}$ denote H and also the radicals $R^{12}$ in each case denote $CH_3$, as hydrochloride, wherein $R^0$ and $R^3$ together denote the group $=O$, $R^{6'}$ denotes the group $OCH_3$ and $R^1$, $R^2$, $R^4$ to $R^6$, $R^{4'}$ and $R^{5'}$ denote H and also the radicals $R^{12}$ in each case denote $CH_3$, as well as the corresponding hydrochloride, wherein $R^0$ and $R^3$ together denote the group $=O$, $R^{6'}$ denotes Cl and $R^1$, $R^2$, $R^4$ to $R^6$, $R^{4'}$ and $R^{5'}$ denote H, and also the radicals $R^{12}$ in each case denote $CH_3$, wherein $R^0$ and $R^3$ together denote the group $=O$, $R^{5'}$ and $R^{6'}$ in each case denote the group $OCH_3$, and $R^1$, $R^2$, $R^4$ to $R^6$ and $R^{4'}$ denote H and also the radicals $R^{12}$ in each case denote $CH_3$, as hydrochloride, wherein $R^0$ and $R^3$ together denote the group $=O$, $R^4$, $R^6$ and $R^{6'}$ in each case denote the group $OCH_3$, and $R^1$, $R^2$, $R^5$, $R^{4'}$ and $R^{5'}$ denote H and also the radicals $R^{12}$ in each case denote $CH_3$, as hydrochloride, wherein $R^0$ denotes OH, $R^3$ denotes H, $CH_3$, unbranched $C_3H_7$, unbranched $C_5H_{11}$, cyclohexyl, phenyl or benzyl, and $R^1$, $R^2$, $R^4$ to $R^6$ and $R^{4'}$ to $R^{6'}$ denote H and also the radicals $R^{12}$ in each case denote $CH_3$, as well as the corresponding hydrochlorides, wherein $R^0$ denotes OH, $R^3$ denotes $C_2H_5$, and $R^1$, $R^2$, $R^4$ to $R^6$ and $R^{4'}$ to $R^{6'}$ denote H and also the radicals $R^{12}$ in each case denote $CH_3$, as well as the corresponding hydrochloride and the corresponding methyliodide, wherein $R^0$ denotes OH, $R^3$ denotes phenyl, $R^6$ denotes Cl, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes Cl, $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ denotes OH, $R^3$ denotes phenyl, $R^{5'}$, $R^{6'}$ in each case denote the group $OCH_3$, $R^1$, $R^2$, $R^4$ to $R^6$ and $R^{4'}$ denote H and also the radicals $R^{12}$ in each case denote $CH_3$, as hydrochloride, wherein $R^0$ denotes OH, $R^3$ denotes phenyl, $R^6$ denotes the group $OCH_3$, $R^1$, $R^2$, $R^4$, $R^5$ and $R^{4'}$ to $R^{6'}$ denote H and also the radicals $R^{12}$ in each case denote $CH_3$, as well as the corresponding hydrochloride, wherein $R^0$ denotes OH, $R^3$ denotes phenyl, $R^{6'}$ denotes the group $OCH_3$, $R^1$, $R^2$, $R^4$ to $R^6$, $R^{4'}$ and $R^{5'}$ denote H and also the radicals $R^{12}$ in each case denote $CH_3$, as well as the corresponding hydrochloride and the corresponding methyliodide, wherein $R^0$ denotes OH, $R^3$ denotes phenyl, $R^6$ and $R^{6'}$ in each case denote the group $OCH_3$, $R^1$, $R^2$, $R^4$, $R^5$, $R^{4'}$ and $R^{5'}$ denote H and also the radicals $R^{12}$ in each case denote $CH_3$, as well as the corresponding hydrochloride, wherein $R^0$ denotes OH, $R^{6'}$ denotes $OCH_3$, $R^1$ to $R^6$, $R^{4'}$ and $R^{5'}$ denote H and also the radicals $R^{12}$ in each case denote $CH_3$, as well as the corresponding hydrochloride, wherein $R^0$, $R^1$, $R^2$ the radicals $R^4$ to $R^6$, the radicals $R^{4'}$ to $R^{6'}$ in each case denote H, the radical $R^3$ denotes phenyl and also the radicals $R^{12}$ in each case denote $CH_3$, as well as the corresponding hydrochloride, and wherein $R^1$, $R^2$, the radicals $R^4$ to $R^6$, the radicals $R^{4'}$ to $R^{6'}$ in each case denote H, the radical $R^3$ and $R^0$ together denote the group $=CHR^{11}$ and also the radical $R^{11}$ and in each case the radicals $R^{12}$ denote $CH_3$, as hydrochloride.

The invention furthermore provides for the use of at least one substituted 3-amino-2-benzyl-1-phenylpropane derivative of the general formula I and/or their enantiomers, diastereomers, bases or salts of physiologically compatible acids for preparing a pharmaceutical product for treating urinary incontinence, inflammations, allergies, depression, drug or alcohol misuse, gastritis, diarrhea, cardiovascular conditions, respiratory conditions, coughing, psychogenic disorders or epilepsy.

In order to prepare appropriate pharmaceutical formulations, there are used in addition to at least one substituted 3-amino-2-benzyl-1-phenylpropane derivative of the general formula I, also excipients, fillers, solvents, diluents, dyes and/or binders. The choice of auxiliaries, as well as the amounts thereof to be used, depends on whether the pharmaceutical product is to be administered orally, intravenously, intraperitoneally, intradermally, intramuscularly, intranasally, buccally or topically, for example to treat infections of the skin, mucous membranes or eyes. For oral application suitable preparations are in the form of tablets, sugar-coated tablets, capsules, granules, drops, ointments and syrups, while for parenteral, topical and inhalative application suitable preparations are in the form of solutions, suspensions, easily reconstitutable dry preparations, as well as sprays.

Compounds according to the invention of the general formula I in a depot in dissolved form or in plaster, optionally with the addition of agents promoting skin penetration, are suitable percutaneous application preparations. Preparations suitable for oral or percutaneous administration can provide for the delayed release of the compounds of formula I according to the invention.

The amount of active substance to be administered to the patient varies depending on the patient's weight, method of application, medical indications and the severity of the condition. Normally 50 to 500 mg/kg of at least one 3-amino-2-benzyl-1-phenylpropane derivative of the general formula I are administered.

EXAMPLES

The following examples serve to illustrate the invention without however restricting the general scope thereof.

The yields of the prepared compounds are not optimized.

All melting points are uncorrected.

Unless otherwise specified, petroleum ether having a boiling point range of 50–70° C. was used. The expression 'ether' denotes diethyl ether.

Silica gel 60 (0.040–0.063 mm) from E. Merck, Darmstadt, was used as stationary phase for the column chromatography.

The thin-layer chromatographic investigations were carried out with HPTLC-prepared plates, silica gel 60 F 254, from E. Merck, Darmstadt.

The racemate separations were carried out on a Chiracel OD column.

The mixing ratios of the solvent systems for all chromatographic investigations are specified in volume/volume.

Example 1

(2RS)-2-benzyl-3-dimethylamino-1-(3-methoxyphenyl)-propan-1-one hydrochloride $1^{st}$ Stage 1-(3-methoxyphenyl)-3-phenylpropan-1-ol 19.1 ml (0.14 mole) of 2-phenylethyl bromide were dissolved in 100 ml of ether and added dropwise to a suspension of 3.4 g (0.14 mole) of magnesium in 300 ml of ether. The reaction solution was next stirred for one hour at 40° C. and then cooled to 0° C. 20.4 g (0.15 mole) of 3-methoxybenzaldehyde in 100 ml of ether were added while cooling with ice and the reaction solution was stirred overnight at 20° C. 150 ml of a 20% ammonium chloride solution was then added at 0° C. to the reaction solution. The reaction solution was extracted three times with 200 ml of ether each time and the combined ether extracts were dried over sodium sulfate. The solvent was removed in vacuo. After drying, 28.5 g (98%) of 1-(3-methoxyphenyl)-3-phenylpropan-1-ol were obtained as a grey oil.

$2^{nd}$ Stage 1-(3-methoxyphenyl)-3-phenylpropan-1-one 14.9 g (0.05 mole) of potassium dichromate in a mixture of 50 ml of water and 10 ml of concentrated sulfuric acid were added to a solution of 34 g (0.14 mole) of 1-(3-methoxyphenyl)-3-phenylpropan-1-ol in 500 ml of ether while cooling with ice and stirred overnight at 20° C. The aqueous, green phase was separated and extracted twice with 100 ml of ether each time. The combined ether extracts were dried over sodium sulfate and the solvent was then removed in vacuo. 28.0 g (83%) of the compound 1-(methoxyphenyl)-3-phenylpropan-1-one were obtained as a yellow oil, which was reacted further without prior purification.

$3^{rd}$ Stage (2RS)-2-benzyl-3-dimethylamino-1-(3-methoxyphenyl)propan-1-one hydrochloride 28 g (0.12 mole) of 1-(3-methoxyphenyl)-3-phenylpropan-1-one were dissolved in 200 ml of acetonitrile, following which 11.3 g (0.12 mole) of the iminium salt of paraformaldehyde and dimethylamine hydrochloride were added under a nitrogen atmosphere. The reaction mixture was then heated for one hour at 60° C. and afterwards cooled to 20° C. The product partially precipitates on stirring overnight. The solvent was removed in vacuo and the crude product was dissolved in water. Sodium bicarbonate was added to the aqueous solution until the pH was 8 and the solution was then extracted three times with ether. The ether extracts were combined, dried over sodium sulfate and the ether was distilled off. The (2RS)-2-benzyl-3-dimethylamino-1-(3-methoxyphenyl)-propan-1-one was dissolved in 100 ml of methyl ethyl ketone and ethereal HCl solution was added until the pH was 1. The resultant precipitate was suction filtered, washed with ether and dried in vacuo; 2-benzyl-3-dimethylamino-1-(3-methoxyphenyl)-propan-1-one hydrochloride was obtained in a yield of 33.0 g (83%) with a melting point of 130° C.

Example 2

(2RS)-1-(3-benzyloxyphenyl)-2-dimethylaminomethyl-3-phenylpropan-1-one hydrochloride The synthesis was carried out according to the procedure of Example 1, except that 60.0 g (0.24 mole) of 3-benzyloxybenzaldehyde were used instead of 3-methoxybenzaldehyde. The reaction steps involving Grignard reaction, oxidation and Mannich reaction led via the three stages to a total yield of 48.0 g (53%) of 1-(3-benzyloxyphenyl)-2-dimethylaminomethyl-3-phenylpropan-1-one hydrochloride with a melting point of 147° C.

Example 3

(3RS)-2-benzyl-1-(4-chlorophenyl)-3-dimethylaminopropan-1-one hydrochloride

The synthesis was carried out according to the procedure of Example 1, except that 16.9 g (0.12 mole) of 4-chlorobenzaldehyde were used instead of 3-methoxybenzaldehyde. The reaction steps involving Grignard reaction, oxidation and Mannich reaction led to a total yield of 12.0 g (47%) of (3RS)-2-benzyl-1-(4-chlorophenyl) 3-dimethylaminopropan-1-one hydrochloride with a melting point of 164° C.

Example 4

(2RS)-3-dimethylamino-2-(4-methoxybenzyl)-1-(3-methoxyphenyl)-propan-1-one hydrochloride The synthesis was carried out according to the procedure of Example 1, except that 30.1 g (0.14 mole) of 2-(4-methoxyphenyl)-ethyl bromide were used instead of 2-phenylethyl bromide. The reaction steps involving Grignard reaction, oxidation and Mannich reaction led to a total yield of 10.5 g (29%) of (2RS)-3-dimethylamino-2-(4-methoxybenzyl)-1-(3-methoxyphenyl)-propan-1-one hydrochloride with a melting point of 134° C.

Example 5

(2RS)-2-benzyl-3-dimethylamino-1-(3-trifluoromethylphenyl)-propan-1-one hydrochloride The synthesis was carried out according to the procedure of Example 1, except that 25.0 g (0.14 mole) of 3-trifluoromethylbenzaldehyde were used instead of 3-methoxybenzaldehyde. The reaction steps involving Grignard reaction, oxidation and Mannich reaction led to a total yield of 21.1 g (41%) of (2RS)-2-benzyl-3-dimethylamino-1-(3-trifluoromethylphenyl)-propan-1-one hydrochloride with a melting point of 104° C.

Example 6

(2RS)-2-benzyl-3-dimethylamino-1-(3-hydroxyphenyl)-propan-1-one hydrochloride

The synthesis of the compound was carried out in four stages. The first three stages were carried out according to the procedure of Example 1, with an identical molar ratio. The fourth reaction step involved the splitting of the methyl ether of the compound (2RS)-2-benzyl-3-dimethylamino-1-(3-hydroxyphenyl)-propan-1-one hydrochloride with methionine and methanesulfonic acid. For this purpose 10.0 g (0.03 mole) of the methyl ether were dissolved in 3.2 ml (0.033 mole) of methanesulfonic acid and heated with 4.5 g (0.6 mole) of methionine for two hours at 75° C. The reaction mixture was then cooled to room temperature, stirred overnight, the methanesulfonic acid was removed in vacuo, and the residue was purified by column chromatography using ethanol. The yield was 0.8 g (2.4 mmole, 8%) of (2RS)-2-benzyl-3-dimethylamino-1-(3-hydroxyphenyl)-propan-1-one hydrochloride with a melting point of 169° C.

Example 7

(2RS)-2-benzyl-1-(3,5-dimethoxyphenyl)-3-dimethylamino-propan-1-one hydrochloride The synthesis was carried out according to the procedure of Example 1, except that 5.0 g (0.03 mole) of 3,5-dimethoxybenzaldehyde were used instead of 3-methoxybenzaldehyde. The reaction steps involving Grignard reaction, oxidation and Mannich reaction led to a total yield of 1.3 g (12%) of (2RS)-2-benzyl-1-(3,5-dimethoxyphenyl)-3-dimethylaminopropan-1-one hydrochloride with a melting point of 151° C.

Example 8

(2RS)-2-benzyl-1-(2,5-dimethoxyphenyl)-3-dimethylaminopropan-1-one hydrochloride The synthesis was carried out according to the procedure of Example 1, except that 12.5 g (0.075 mole) of 2,5-dimethoxybenzaldehyde were used instead of 3-methoxybenzaldehyde. The reaction steps involving Grignard reaction, oxidation and Mannich reaction led to a total yield of 4.3 g (15%) of (2RS)-2-benzyl-1-(2,5-dimethoxyphenyl)-3-dimethylaminopropan-1-one hydrochloride with a melting point of 149° C.

Example 9

(2RS)-2-benzyl-1-(2,3-dimethoxyphenyl)-3-dimethylaminopropan-1-one hydrochloride The synthesis was carried out according to the procedure of Example 1, except that 12.5 g (0.075 mole) of 2,3-dimethoxybenzaldehyde were used instead of 3-methoxybenzaldehyde. The reaction steps involving Grignard reaction, oxidation and Mannich reaction led to a total yield of 3.5 g (14%) of 2-benzyl-1-(2,3-dimethoxyphenyl)-3-dimethylaminopropan-1-one hydrochloride. The compound is hygroscopic.

Example 10

(+)-(R)-2-benzyl-3-dimethylamino-1-(3-methoxyphenyl)-propan-1-one hydrochloride

The synthesis was carried out according to the procedure of Example 1, with an identical molar ratio. The racemate thus obtained was then separated into the enantiomers by chromatography on a Chiracel OD column with ethanol, ethyl acetate and saturated aqueous ammonia solution in a ratio of 1/1/0.05, and (+)-(R)-2-benzyl-3-dimethylamino-1-(3-methoxyphenyl)-propan-1-one hydrochloride was obtained.

Example 11

(−)-(S)-2-benzyl-3-dimethylamino-1-(3-methoxyphenyl)-propan-1-one hydrochloride

The synthesis was carried out according to the procedure of Example 1, with an identical molar ratio. The racemate thus obtained was then separated into the enantiomers by chromatography on a Chiracel OD column with ethanol, ethyl acetate and saturated aqueous ammonia solution in a ratio of 1/1/0.05, and (−)-(S)-2-benzyl-3-dimethylamino-1-(3-methoxyphenyl)-propan-1-one hydrochloride was obtained.

Example 12

(2RS)-2-benzyl-1-(2,3-dichlorophenyl)-3-dimethylaminopropan-1-one hydrochloride

The synthesis was carried out according to the procedure of Example 1, except that 10.0 g (0.056 mole) of 2,3-dichlorobenzaldehyde were used instead of 3-methoxybenzaldehyde. The reaction steps involving Grignard reaction, oxidation and Mannich reaction led to a total yield of 0 17 g (1%) of (2RS)-2-benzyl-1-(2,3-dichlorophenyl)-3-dimethylaminopropan-1-one hydrochloride with a melting point of 114° C.

Example 13

(2RS)-2-benzyl-1-(2,5-dichlorophenyl)-3-dimethylaminopropan-1-one hydrochloride

The synthesis was carried out according to the procedure of Example 1, except that 5.0 g (0.028 mole) of 2,5- dichlorobenzaldehyde were used instead of 3-methoxybenzaldehyde. The reaction steps involving Grignard reaction, oxidation and Mannich reaction led to a total yield of 1.4 g (14%) of (2RS)-2-benzyl-1-(2,4-dichlorophenyl)-3-dimethylaminopropan-1-one hydrochloride with a melting point of 140° C.

Example 14

(2RS)-2-benzyl-3-dimethylamino-1-(2,3,4-trimethoxyphenyl)-propan-1-one hydrochloride The synthesis was carried out according to the procedure of Example 1, except that 10.0 g (0.05 mole) of 2,3,4-trimethoxybenzaldehyde were used instead of 3-methoxybenzaldehyde. The reaction steps involving Grignard reaction, oxidation and Mannich reaction led to a total yield of 6.2 g (26%) of (2RS)-2-benzyl-3-dimethylamino-1-(2,3,4-trimethoxyphenyl)-propan-1-one hydrochloride with a melting point of 141° C.

Example 15

(2RS)-2-benzyl-3-dimethylamino-1-(3,4,5-trimethoxyphenyl)-propan-1-one hydrochloride The synthesis was carried out according to the procedure of Example 1, except that 10.0 g (0.05 mole) of 3,4,5-trimethoxybenzaldehyde were used instead of 3-methoxybenzaldehyde. The reaction steps involving Grignard reaction, oxidation and Mannich reaction led to a total yield of 14.5 g (60%) of (2RS)-2-benzyl-3-dimethylamino-1-(3,4,5-trimethoxyphenyl)-propan-1-one hydrochloride with a melting point of 125° C.

Example 16

(2RS)-2-benzyl-1-(2,5-dihydroxyphenyl)-3-dimethylaminopropan-1-one hydrochloride The synthesis was carried out according to the procedure of Example 6, except that 12.5 g (0.075 mole) of 2,5-dimethoxybenzaldehyde were used instead of 3-methoxybenzaldehyde. The reaction steps involving Grignard reaction, oxidation, Mannich reaction and ether cleavage led to a total yield of 0.6 g (2%) of (2RS)-2-benzyl-1-(2,5-dihydroxyphenyl)-3-dimethylaminopropan-1-one hydrochloride with a melting point of 177° C.

Example 17

(2RS)-2-benzyl-3-dimethylamino-1-(2-methoxyphenyl)-propan-1-one hydrochloride

The synthesis was carried out according to the procedure of Example 1, except that 50.0 g (0.37 mole) of 2-methoxybenzaldehyde were used instead of 3-methoxybenzaldehyde. The reaction steps involving Grignard reaction, oxidation and Mannich reaction led to a total yield of 4.7 g (3%) of (2RS)-2-benzyl-3-dimethylamino-1-(2-methoxyphenyl)-propan-1-one hydrochloride with a melting point of 159° C.

Example 18

(2RS)-2-benzyl-3-dimethylamino-1-naphthalen-2-yl-propan-1-one hydrochloride

The synthesis was carried out according to the procedure of Example 1, except that 10.0 g (0.064 mole) of naphthalen-2-carbaldehyde were used instead of 3-methoxybenzaldehyde. The reaction steps involving Grignard reaction, oxidation and Mannich reaction led to a total yield of 3.7 g (15%) of (2RS)-2-benzyl-3-dimethylamino-1-naphthalen-2-yl-propan-1-one hydrochloride with a melting point of 135.3° C.

Example 19

(2RS)-2-benzyl-3-dimethylamino-1-phenanthren-3-yl-propan-1-one hydrochloride

The synthesis was carried out according to the procedure of Example 1, except that 5.0 g (0.024 mole) of phenanthrene-2-carbaldehyde were used instead of 3-methoxybenzaldehyde. The reaction steps involving Grignard reaction, oxidation and Mannich reaction led to a total yield of 1.4 g (14%) of (2RS)-2-benzyl-3-dimethylamino-1-phenanthren-3-yl-propan-1-one hydrochloride with a melting point of 138.7° C.

Example 20

(2RS)-2-benzyl-3-dimethylamino-1-(2-hydroxyphenyl)-propan-1-one hydrochloride

The synthesis was carried out according to the procedure of Example 6, except that 2-methoxybenzaldehyde was used instead of 3-methoxybenzaldehyde. The reaction steps involving Grignard reaction, oxidation, Mannich reaction and ether cleavage led to a total yield of 2.0 g (2%) of (2RS)-2-benzyl-3-dimethylamino-1-(2-hydroxyphenyl)-propan-1-one hydrochloride with a melting point of 123° C.

Example 21

(2RS)-2-benzyl-3-dimethylamino-1-(2-fluorophenyl)-propan-1-one hydrochloride

The synthesis was carried out according to the procedure of Example 1, except that 25.0 g (0.2 mole) of 2-fluorobenzaldehyde were used instead of 3-methoxybenzaldehyde. The reaction steps involving Grignard reaction, oxidation and Mannich reaction led to a total yield of 0.37 g (1%) of 2-benzyl-3-dimethylamino-1-(2-fluorophenyl)-propan-1-one hydrochloride with a melting point of 127° C.

Example 22

(2RS)-2-benzyl-3-dimethylamino-1-(3-methylsulfanylphenyl)-propan-1-one hydrochloride The synthesis was carried out according to the procedure of Example 1. 5.0 g (0.025 mole) of 3-bromothioanisole and 6.7 g (0.025 mole) of 3-phenylpropionaldehyde were used as educts. The reaction steps involving Grignard reaction, oxidation and Mannich reaction led to a total yield of 0.4 g (6%) of (2RS)-2-benzyl-3-dimethylamino-1-(3-methylsulfanylphenyl)-propan-1-one hydrochloride with a melting point of 118° C.

Example 23

(2RS)-3-dimethylamino-2-(3-methylbenzyl)-1(3-methoxyphenyl)-propan-1-one hydrochloride The synthesis was carried out according to the procedure of Example 1, except that 5.2 g (0.026 mole) of 1-(2-bromoethyl)-3-methylbenzene were used instead of

Example 24

(2RS)-2-benzyl-3-dimethylamino-1-(2-hydroxy-5-methoxyphenyl)-propan-1-one hydrochloride The synthesis was carried out according to the procedure of Example 8, followed by ether cleavage according to Example 6. 1.5 g (6%) of (2RS)-2-benzyl-3-dimethylamino-1-(2-hydroxy-5-methoxyphenyl)-propan-1-one hydrochloride were obtained with a melting point of 90° C.

Example 25

(2RS)-3-dimethylamino-2-(3-methoxybenzyl)-1-(3-methoxyphenyl)-propan-1-one hydrochloride The synthesis was carried out according to the procedure of Example 1, except that 15.3 g (0.07 mole) of 1-(2-bromoethyl)-3-methoxybenzene were used instead of 2-phenylethyl bromide. The reaction steps involving Grignard reaction, oxidation and Mannich reaction led to a total yield of 2.3 g (5%) of (2RS)-3-dimethylamino-2-(3-methoxybenzyl)-1-(3-methoxyphenyl)-propan-1-one hydrochloride.

Example 26

(2RS)-3-(2-benzyl-3-dimethylaminopropionyl)-benzonitrile hydrochloride

The synthesis was carried out according to the procedure of Example 1, except that 3.0 g (0.038 mole) of 3-cyanocarbaldehyde were used instead of 3-methoxybenzaldehyde. The reaction steps involving Grignard reaction, oxidation and Mannich reaction led to a total yield of 1.3 g (10%) of (2RS)-3-(2-benzyl-3-dimethylaminopropionyl)-benzonitrile hydrochloride with a melting point of 154° C.

Example 27

(2RS)-2-benzyl-1-biphenyl-3-yl-3-dimethylaminopropan-1-one hydrochloride

The synthesis was carried out according to the procedure of Example 1, 5.0 g (0.021 mole) of 3-bromobiphenyl and 2.8 g (0.021 mole) of 3-phenylpropionaldehyde being used. The reaction steps involving Grignard reaction, oxidation and Mannich reaction led to a total yield of 0.7 g (8%) of 2-benzyl-1-biphenyl-3-yl-3-dimethylaminopropan-1-one hydrochloride with a melting point of 162° C.

Example 28

(2RS)-2-benzyl-3-dimethylamino-1-(6-methoxynaphthalen-2-yl)-propan-1-one hydrochloride The synthesis was carried out according to the procedure of Example 1, except that 25.0 g (0.134 mole) of 6-methoxynaphthalen-2-carbaldehyde were used instead of 3-methoxybenzaldehyde. The reaction steps involving Grignard reaction, oxidation and Mannich reaction led to a total yield of 4.3 g (8%) of (2RS)-2-benzyl-3-dimethylamino-1-(6-methoxynaphthalen-2-yl)-propan-1-one hydrochloride with a melting point of 88–95° C.

Example 29

(2RS)-2-benzyl-3-dimethylamino-1-(6-hydroxynaphthalen-2-yl)-propan-1-one hydrochloride The compound was obtained by ether cleavage of (2RS)-2-benzyl-3-dimethylamino-1-(6-methoxynaphthalen-2-yl)propan-1-one hydrochloride from Example 28, according to Example 6. The synthesis led to a yield of 9.5 g (40%) of (2RS)-2-benzyl-3-dimethylamino-1-(6-hydroxynaphthalen-2-yl)-propan-1-one hydrochloride with a melting point of 180–182° C.

Example 30

(2RS)-2-benzyl-1-biphenyl-2-yl-3-dimethylaminopropan-1-one hydrochloride

The synthesis was carried out according to the procedure of Example 1, 5.0 g (0.021 mole) of 2-bromobiphenyl being reacted with 2.8 g (0.021 mole) of 3-phenylpropionaldehyde. The reaction steps involving Grignard reaction, oxidation and Mannich reaction led to a total yield of 2.8 g (35%) of (2RS)-2-benzyl-1-biphenyl-2-yl-3-dimethylaminopropan-1-one hydrochloride with a melting point of 134–134.8° C.

Example 31

(2RS)-2-benzyl-1-(2-chloro-4-fluorophenyl)-3-dimethylaminopropan-1-one hydrochloride The synthesis was carried out according to the procedure of Example 1, except that 5.0 g (0.03 mole) of 2-chloro-4-fluorobenzaldehyde were used instead of 3-methoxybenzaldehyde. The reaction steps involving Grignard reaction, oxidation and Mannich reaction led to a total yield of 2.6 g (24%) of (2RS)-2-benzyl-1-(2-chloro-4-fluorophenyl)-3-dimethylaminopropan-1-one hydrochloride with a melting point of 150.3° C.

Example 32

(2RS)-(2-dimethylaminomethyl-1-[(1RS)-3-(1-hydroxy-3-phenylpropyl)-phenyl]-3-phenylpropan-1-one hydrochloride The synthesis was carried out according to the procedure of Example 1, except that 10.0 g (0.075 mole) of benzene-1,3-dicarbaldehyde were used instead of 3-methoxybenzaldehyde. The reaction steps involving Grignard reaction, oxidation and Mannich reaction led to a total yield of 2.0 g (6%) of (2RS)-(2-dimethylaminomethyl-1-[(1RS)-3-(1-hydroxy-3-phenylpropyl)-phenyl]-3-phenylpropan-1-one hydrochloride with a melting point of 135° C.

Example 33

(+)-(R)-2-benzyl-3-dimethylamino-1-(3-hydroxyphenyl)-propan-1-one hydrochloride

The synthesis was carried out according to Example 1, followed by an ether cleavage according to Example 6 as well as a column chromatography racemate separation with ethanol as eluent. The separation resulted in a total yield of 20 mg (0.5%) of (+)-(R)-2-benzyl-3-dimethylamino-1-(3-hydroxyphenyl)-propan-1-one hydrochloride.

Example 34

(−)-(S)-2-benzyl-3-dimethylamino-1-(3-hydroxyphenyl)-propan-1-one hydrochloride

The synthesis was carried out according to the procedure of Example 1, followed by an ether cleavage according to Example 6 as well as a column chromatography racemate separation with ethanol as eluent. The separation resulted in a total yield of 20 mg (0.5%) of (−)-(S)-2-benzyl-3-dimethylamino-1-(3-hydroxyphenyl)-propan-1-one hydrochloride.

Example 35

(2RS)-3-dimethylamino-2-(2-fluorobenzyl)-1-(3-methoxyphenyl)-propan-1-one hydrochloride The synthesis was carried out according to the procedure of Example 1, except that 5.0 g (0.025 mole) of 1-(2-bromoethyl)-2-fluorobenzene were used instead of 2-phenylethyl bromide. The reaction steps involving Grignard reaction, oxidation and Mannich reaction led to a total yield of 0.6 g (7%) of (2RS)-3-dimethylamino-2-(2-fluorobenzyl)-1-(3-methoxyphenyl)-propan-1-one hydrochloride with a melting point of 111° C.

Example 36

(2RS)-3-dimethylamino-2-(3-fluorobenzyl)-1-(3-methoxyphenyl)-propan-1-one hydrochloride The synthesis was carried out according to the procedure of Example 1, except that 5.0 g (0.025 mole) of 1-(2-bromoethyl)-3-fluorobenzene were used instead of 2-phenylethyl bromide. The reaction steps involving Grignard reaction, oxidation and Mannich reaction led to a total yield of 0.2 g (1%) of (2RS)-3-dimethylamino-2-(3-fluorobenzyl)-1-(3-methoxyphenyl)-propan-1-one hydrochloride with a melting point of 141° C.

Example 37

(2RS)-3-dimethylamino-2-(4-fluorobenzyl)-1-(3-methoxyphenyl)-propan-1-one hydrochloride The synthesis was carried out according to the procedure of Example 1, except that 5.0 g (0.025 mole) of 1-(2-bromoethyl)-4-fluorobenzene were used instead of 2-phenylethyl bromide. The reaction steps involving Grignard reaction, oxidation and Mannich reaction led to a total yield of 0.6 g (7%) of (2RS)-3-dimethylamino-2-(4-fluorobenzyl)-1-(3-methoxyphenyl)-propan-1-one hydrochloride with a melting point of 138° C.

Example 38

Z-(2RS)-(3RS)-2-dimethylaminomethyl-1,3-diphenylpentan-1-one hydrochloride

The compound was not synthesised according to the procedure of Example 1. Instead, an aldol condensation of equimolar amounts of benzaldehyde and acetophenone were first of all carried out to give 1,3-diphenylpropenone:

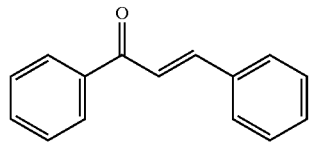

This compound is first of all reacted with an equimolar amount of the cuprate of the ethyl bromide in a 1,4-addition to form the corresponding enolate. The organocopper compound is formed in situ from the Grignard compound of ethyl bromide and magnesium by transmetallation with copper-I iodide.

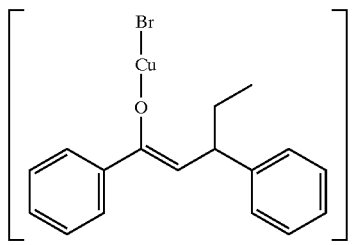

This enolate is reacted further in situ with an equimolar amount of the Eschenmoser salt, stirred overnight at 20° C., and then worked up in the aqueous medium. The aqueous phase is adjusted to the alkaline and the product is extracted with ether. Z-(2RS)-(3RS)-2-dimethylaminomethyl-1,3-diphenylpentan-1-one hydrochloride was then precipitated by adding trimethylsilyl chloride to the free base in methyl ethyl ketone.

2.6 g (71%) of Z-(2RS)-(3RS)-2-dimethylaminomethyl-1,3-diphenylpentan-1-one hydrochloride with a melting point of 177° C. were obtained. The Z-(erythro)-diastereomer was formed exclusively.

Example 39

E-(2RS) -(3RS) -2-dimethylaminomethyl-3-(2-methoxyphenyl)-1,3-diphenylpropan-1-one hydrochloride The synthesis was carried out according to the procedure of Example 38, except that 3-bromoanisol was used instead of ethyl bromide as a component of the cuprate addition. The synthesis led to a total yield of 7.5 g (48%) of E-(2RS)-(3RS)-2-dimethylaminomethyl-3-(3-methoxyphenyl)-1,3-diphenylpropan-1-one hydrochloride with a melting point of 192° C. The E-(threo)-distereomer was formed exclusively.

Example 40

(2RS)-(3RS)-2-dimethylaminomethyl-1,3,3-tris-(3-methoxyphenyl)-propan-1-one hydrochloride The synthesis was carried out according to the procedure of Example 38. The 3-methoxyacetophenone and 3-methoxybenzaldehyde were used in equimolar amounts in the aldol condensation. The chalcone derivative was reacted with 3-bromoanisol in the cuprate addition, followed by reaction with the Eschenmoser salt. The synthesis led to a total yield of 0.3 g (2%) of (2RS)-(3RS)-2-dimethylaminomethyl-1,3,3-tris-(3-methoxyphenyl)-propan-1-one hydrochloride with a melting point of 165.1° C.

Example 41

(2RS)-(3RS)-2-dimethylaminomethyl-1,3-bis-(3-methoxyphenyl)-3-phenylpropan-1-one hydrochloride The synthesis was carried out according to the procedure of Example 38. The 3-methoxyacetophenone and 3-methoxybenzaldehyde were used in equimolar amounts in the aldol condensation. The corresponding chalcone derivative was reacted with bromobenzene in the cuprate addition, followed by reaction with the Eschenmoser salt. The synthesis led to a total yield over the three stages of 4.5 g (17%) of the compound (2RS)-(3RS)-2-dimethylaminomethyl-1,3-bis-(3-methoxyphenyl)-3-phenylpropan-1-one hydrochloride with a melting point of 139.1° C.

Example 42

(2RS)-(3RS)-2-dimethylaminomethyl-1,3-diphenyl-3-p-tolylpropan-1-one hydrochloride The synthesis was carried out according to the procedure of Example 38 and the chalcone derivative was reacted with 4-bromotoluene. The Eschenmoser salt was then added in an equimolar amount. The yield of (2RS)-(3RS)-2-dimethylamino-methyl-1,3-diphenyl-3-p-tolylpropan-1-one hydrochloride was 0.7 g (41%).

Example 43

(Z)-(2RS)-(3RS)-2-dimethylaminomethyl-1-(3-methoxyphenyl)-3,4-diphenylbutan-1-one hydrochloride The synthesis was carried out according to the procedure of Example 38. 3-methoxyacetophenone and benzaldehyde were used in equimolar amounts in the aldol condensation. The chalcone derivative was reacted with benzyl chloride. The yield of (Z)-(2RS)-(3RS)-2-dimethylaminomethyl-1-(3-methoxyphenyl)-3,4-diphenylbutan-1-one hydrochloride was 0.8 g (33%) with a melting point of 81.5° C. The Z-(erythro)-diastereomer was formed exclusively.

Example 44

(2RS)-(3RS)-2-dimethylaminomethyl-1,3,6-triphenylhexan-1-one hydrochloride

The synthesis was carried out according to the procedure of Example 38. The chalcone derivative was reacted with 1-bromo-3-phenylpropane. The Eschenmoser salt was then added in an equimolar amount. The yield of (2RS)-(3RS)-2-dimethylamino-methyl-1,3,6-triphenylhexan-1-one hydrochloride was 0.9 g (44%).

Example 45

(2RS)-(3RS)-2-dimethylaminomethyl-1-(3-methoxyphenyl)-3-phenylpentan-1-one hydrochloride The synthesis was carried out according to the procedure of Example 38. 3-methoxyacetophenone and benzaldehyde were used in equimolar amounts in the aldol condensation. The chalcone derivative was reacted with ethyl bromide in the cuprate addition, which was followed by reaction with the Eschenmoser salt. The synthesis led to a total yield of 0.8 g (7%) of (2RS)-(3RS)-2-dimethylaminomethyl-1-(3-methoxyphenyl)-3-phenylpentan-1-one hydrochloride with a melting point of 89.5° C.

Example 46

(2RS)-(3RS)-2-dimethylaminomethyl-3,3-bis-(3-methoxyphenyl)-1-naphthalen-2-yl-propan-1-one hydrochloride The synthesis was carried out according to the procedure of Example 38. 1-napthalen-2-yl-ethanone and 3-methoxybenzaldehyde were used in equimolar amounts in the aldol condensation. The chalcone derivative was reacted with m-bromoanisol in the cuprate addition. This was followed by reaction with an equimolar amount of Eschenmoser salt. The synthesis over the three stages led to a total yield of 10.3 g (65%) of (2RS)-(3RS)-2-dimethylaminomethyl-3,3-bis-(3-methoxyphenyl)-1-naphthalen-2-yl-propan-1-one hydrochloride with a melting point of 192.8° C.

Example 47

E-(2RS)-(3RS)-3-benzyl-4-dimethylamino-2-(3-methoxyphenyl)-butan-2-ol hydrochloride The synthesis was carried out up to the third stage according to the procedure of Example 1. This was then followed by the reaction of 10 g (0.03 mole) of 2-benzyl-3-dimethylamino-1-(3-methoxyphenyl)-propan-1-one with 10 g (0.069 mole) of methyl magnesium iodide to form E-(2RS)-(3RS)-3-benzyl-4-dimethyl-amino-2-(3-methoxyphenyl)-butan-2-ol. The Grignard reagent was prepared from methyl iodide and magnesium in 200 ml of ether, cooled to 0° C. and the ketone 2-benzyl-3-dimethylamino-1-(3-methoxyphenyl)-propan-1-one, dissolved in 200 ml of ether, was added dropwise within 30 minutes. The reaction mixture was then stirred overnight at 20° C., a 20% ammonium chloride solution was added to the excess Grignard reagent, and the whole was extracted with 900 ml of ether. The solvent was distilled off, the residue was dissolved in methyl ethyl ketone, and trimethylsilyl chloride was added in excess. On adding ether a white precipitate formed, which was filtered off under suction, washed with ether and dried. The synthesis led to a yield of 8.4 g (80%) of E-(2RS)-(3RS)-3-benzyl-4-dimethylamino-2-(3-methoxyphenyl)-butan-2-ol hydrochloride with a melting point of 186° C.

Example 48

E-(2RS)-(3RS)-2-benzyl-1-dimethylamino-3-(3-methoxyphenyl)-pentan-3-ol hydrochloride The synthesis was carried out up to the third stage according to the procedure of Example 1. The compound 2-benzyl-3-dimethylamino-1-(3-methoxyphenyl)-propan-1-one was then reacted with ethyl magnesium bromide. The Grignard reagent was prepared in this example from 1.2 g (11 mmole) of ethyl bromide in 50 ml of ether and 0.27 g (11 mmole) of magnesium, and reacted with 2.5 g (7.5 mmole) of 2-benzyl-3-dimethylamino-1-(3-methoxyphenyl)-propan-1-one at 0° C. The yield of E-(2RS)-(3RS)-2-benzyl-1-dimethylamino-3-(3-methoxyphenyl)-pentan-3-ol hydrochloride was 1.87 g (71%) with a melting point of 186.0° C.

Example 49

E-(2RS)-(3RS)-3-benzyl-4-dimethylamino-2-(3-methoxyphenyl)-1-phenylbutan-2-ol hydrochloride The synthesis was carried out up to the third stage according to the procedure of Example 1. The compound 2-benzyl-3-dimethylamino-1-(3-methoxyphenyl)-propan-1- one was then reacted with benzyl magnesium bromide. The Grignard reagent was prepared from 1.5 g (8.75 mmole) of benzyl bromide in 50 ml of ether and 0.21 g (8.75 mmole) of magnesium and reacted with 2.5 g (7.5 mmole) of 2-benzyl-3-dimethylamino-1-(3-methoxyphenyl)-propan-1-one at 0° C. The yield of E-(2RS)-(3RS)-3-benzyl-4-dimethylamino-2-(3-methoxyphenyl)-1-phenylbutan-2-ol hydrochloride was 0.94 g (29%) with a melting point of 208.7° C.

Example 50

Z-(1RS)-(2RS)-2-benzyl-1-(4-chlorophenyl)-3-dimethylamino-1-(3-methoxyphenyl)-propan-1-ol hydrochloride The synthesis was carried out up to the third stage according to the procedure of Example 3. The compound (3RS)-2-benzyl-1-(4-chlorophenyl)-3-dimethylamino-propan-1-one was then reacted with m-anisol magnesium bromide. The Grignard reagent was prepared from 3.7 g (20 mmole) of m-bromoanisole in 5 ml of tetrahydrofuran (THF) with 0.5 g (20 mmole) of magnesium and was reacted at 0° C. with 5 g (15 mmole) of 2-benzyl-3-dimethylamino-1-(3-methoxyphenyl)-propan-1-one in 10 ml (THF). The yield of Z-(1RS)-(2RS)-2-benzyl-1-(4-chlorophenyl)-3-dimethylamino-1-(3-methoxyphenyl)-propan-1-ol hydrochloride was 2.5 g (41%) with a melting point of 145° C.

Example 51

E-(2RS)-(3RS)-2-benzyl-3-(4-chlorophenyl)-1-dimethylamino-pentan-3-ol hydrochloride The synthesis was carried out up to the third stage according to the procedure of Example 3. The compound (3RS)-2-benzyl-1-(4-chlorophenyl)-3-dimethylamino-propan-1-one was then reacted with ethyl magnesium bromide. The Grignard reagent was prepared from 1.5 g (20 mmole) of ethyl bromide in 10 ml of ether and 0.5 g (20 mmole) of magnesium and was reacted at 0° C. with 5 g (15 mmole) of (3RS)-2-benzyl-1-(4-chlorophenyl)-3-dimethylamino-propan-1-one in 10 ml of ether. The yield of E-(2RS)-(3RS)-2-benzyl-3-(4-chlorophenyl)-1-dimethylamino-pentan-3-ol hydrochloride was 3.5 g (53%) with a melting point of 237° C.

Example 52

E-(2RS)-(4RS)-3-benzyl-2-(3-benzyloxyphenyl)-4-dimethylamino-butan-2-ol hydrochloride The synthesis was carried out up to the third stage according to the procedure of Example 2. The compound 1-(3-benzyloxyphenyl)-2-dimethylaminomethyl-3-phenyl-propan-1-one was then reacted with methyl magnesium iodide. The Grignard reagent was prepared from 3.2 g (22.5 mmole) of methyl iodide in 50 ml of ether and 0.45 g (20 mmole) of magnesium, and reacted with 5 g (12.2 mmole) of 1-(3-benzyloxyphenyl)-2-dimethylaminomethyl-3-phenylpropan-1-one in 100 ml of ether at 0° C. The yield was 4.2 g (81%) with a melting point of 215° C.

Example 53

E-(2RS)-3(RS)-2-benzyl-3-(3-benzyloxyphenyl)-1-dimethylamino-pentan-3-ol hydrochloride The synthesis was carried out up to the third stage according to the procedure of Example 2. The compound 1-(3-benzyloxyphenyl)-2-dimethylaminomethyl-3-phenylpropan-1-one was then reacted with ethyl magnesium bromide. The Grignard reagent was prepared from 1.5 g (14.0 mmole) of ethyl bromide in 50 ml of ether and 0.27 g (11.0 mmole) of magnesium, and reacted with 2.5 g (7.5 mmole) of 1-(3-benzyloxyphenyl)-2-dimethylaminomethyl-3-phenylpropan-1-one in 100 ml of ether at 0° C. The yield of E-(2RS)-3(RS)-2-benzyl-3-(3-benzyloxy-phenyl)-1-dimethylamino-pentan-3-ol hydrochloride was 1.8 g (60%) with a melting point of 233° C.

Example 54

E-(2RS)-(3RS)-2-dimethylaminomethyl-3-(3-methoxyphenyl)-1-phenylhex-5-en-3-ol hydrochloride The synthesis was carried out according to the procedure of Example 47. The Grignard reagent was prepared from 2.3 g (19.0 mmole) of allyl bromide in 50 ml of ether and 0.41 g (18.0 mmole) of magnesium, and reacted with 5 g (15.0 mmole) of 2-benzyl-3-dimethylamino-1-(3-methoxyphenyl)-propan-1-one at 0° C. The yield of E-(2RS)-(3RS)-2-dimethylaminomethyl-3-(3-methoxyphenyl)-1-phenylhex-5-en-3-ol hydrochloride was 0.6 g (9%) with a melting point of 140–145° C.

Example 55

E-(2RS)-(3RS)-2-benzyl-3-dimethylamino-1,1-bis-(3-methoxyphenyl)-propan-1-ol hydrochloride The synthesis was carried out according to the procedure of Example 47. The Grignard reagent was prepared from 6.2 g (34 mmole) of 3-bromoanisole in 100 ml of tetrahydrofuran and 0.5 g (20 mmole) of magnesium, and reacted with 5 g (15 mmole) of 2-benzyl-3-dimethylamino-1-(3-methoxyphenyl)-propan-1-one at 0° C. The yield of E-(1RS)-(2RS)-2-benzyl-3-dimethylamino-1,1-bis-(3-methoxyphenyl)-propan-1-ol hydrochloride was 4.6 g (71%) with a melting point of 177–179° C.

Example 56

(2RS)-(3RS)-3-benzyl-4-dimethylamino-1,1,1-trifluoro-2-(3-methoxyphenyl)-butan-1-ol The synthesis was carried out up to the third stage according to the procedure of Example 1. 0.97 g (6.8 mmole) of trifluoromethyl trimethylsilane in 25 ml of tetrahydrofuran was added at −10° C. to 2.0 g of 2-benzyl-3-dimethylamino-1-(3-methoxyphenyl)-propan-1-one and the whole was stirred for one hour. The solution was then heated to room temperature and stirred overnight. The reaction mixture was worked up according to the procedure of Example 1. The yield of (2RS)-(3RS)-3-benzyl-4-dimethylamino-1,1,1-trifluoro-2-(3-methoxyphenyl)-butan-2-ol was 1.2 g (3 mmole, 44%) as free base.

Example 57

E-(2RS)-(3RS)-3-(2-benzyl-3-dimethylamino-1-hydroxypropyl)-phenol hydrochloride

The synthesis was carried out up to the third stage according to the procedure of Example 1. 2.2 g (5.8 mmole) of 2-benzyl-3-dimethylamino-1-(3-benzyloxyphenyl)-propan-1-one were then hydrogenated for 24 hours with hydrogen at a pressure of 1 bar in ethanol in the presence of 0.2 g of Pd/C (10%). The catalyst was then filtered off and the solvent was removed in vacuo. 0.9 g (30%) of E-(1RS)-(2RS)-3-(2-benzyl-3-dimethylamino-1-hydroxypropyl)-phenol hydrochloride was isolated after precipitation with HCl, and had a melting point of 108° C.

Example 58

E-(2RS)-(3RS)-3-(2-benzyl-3-dimethylamino-1-hydroxy-1-methylproply)-phenol hydrochloride The synthesis was carried out according to the procedure of Example 52, followed by ether cleavage with hydrogen according to Example 57. The yield of E-(2RS)-(3RS)-3-(2-benzyl-3-dimethylamino-1-hydroxy-1-methylpropyl)-phenol hydrochloride was 1.2 g (44%) with a melting point of 196° C.

Example 59

E-(2RS)-3(RS)-3-(2-benzyl-3-dimethylamino-1-ethyl-1-hydroxy-propyl)-phenol hydrochloride The synthesis was carried out according to the procedure of Example 53, followed by ether cleavage with hydrogen according to Example 57. The yield of E-(2RS)-3(RS)-3-(2-benzyl-3-dimethylamino-1-ethyl-1-hydroxypropyl)-phenol hydrochloride was 1.2 g (44%) with a melting point of 158.7° C.

Example 60

(E)-(2RS)-(3RS)-3-benzyl-2-(4-chlorophenyl)-4-dimethylamino-1-phenylbutan-2-ol hydrochloride The synthesis was carried out up to the third stage according to the procedure of Example 3. 2.6 g of (3RS)-2-benzyl-1-(4-chlorophenyl)-3-dimethylamino-propan-1-one hydrochloride were added at 10° C. to a solution of 0.5 g (0.02 mole) of magnesium and 2.3 ml (0.02 mmole) of benzyl chloride in 40 ml of ether. The solution was then heated to room temperature and stirred overnight. The reaction mixture was worked up according to the procedure of Example 1. The yield of (E)-(2RS)-(3RS)-3-benzyl-2-(4-chlorophenyl)-4-dimethylamino-1-phenyl-butan-2-ol hydrochloride was 0.52 g (12%) with a melting point of 226.8° C.

Example 61

(Z)-(2RS)-(3RS)-3-benzyl-2-(4-chlorophenyl)-4-dimethylamino-1-phenylbutan-2-ol hydrochloride The synthesis was carried out up to the third stage according to the procedure of Example 3. 2.6 g of (3RS)-2-benzyl-1-(4-chlorophenyl)-3-dimethylamino-propan-1-one hydrochloride were added at 10° C. to a solution of 0.5 g (0.02 mole) of magnesium and 2.3 ml (0.02 mmole) of benzyl chloride in 40 ml of ether. The solution was then heated to room temperature and stirred overnight. The reaction mixture was worked up according to the procedure of Example 1. The yield of (Z)-(2RS)-(3RS)-3-benzyl-2-(4-chlorophenyl)-4-dimethylamino-1-phenylbutan-2-ol hydrochloride was 0.2 g (5%) with a melting point of 266.1° C.

Example 62

(2RS)-3-[1-(1-benzyl-2-dimethylaminoethyl)-vinyl]-phenol hydrochloride

The synthesis was carried out up to the fourth stage according to the procedure of Example 47. 0.5 g (1.6 mmole) of E-(2RS)-(3RS)-3-benzyl-4-dimethylamino-2-(3-methoxyphenyl)-butan-2-ol was then stirred with 15 ml of 33% HBr/glacial acetic acid solution at 20° C. for 3 days. The solvent and excess HBr were then distilled off in vacuo and the residue was taken up in 25 ml of ethyl methyl ketone and heated for 6.5 hours at 70° C. The solvent was then removed in vacuo, the residue was taken up in methyl ethyl ketone, and the free base was precipitated as hydrochloride with trimethylsilyl chloride. The yield of (2RS)-3-[1-(benzyl-2-dimethylaminoethyl)-vinyl]-phenol hydrochloride was 0.19 g (38%).

Example 63

Z/E-(2RS)-3-[1-(1-benzyl-2-dimethylaminoethyl)-propenyl]-phenol hydrochloride

The synthesis was carried out up to the fourth stage according to the procedure of Example 48. 1.0 g (2.75 mmole) of E-(2RS)-(3RS)-2-benzyl-1-dimethylamino-3-(3-methoxyphenyl)-pentan-3-ol as hydrochloride was then stirred with 10 ml of 33% HBr/glacial acetic acid solution for 24 hours at 20° C. The solvent and excess HBr were then removed in vacuo, and the residue was taken up in 25 ml of ethyl methyl ketone and heated for 2 hours at 70° C. The solvent was then distilled off in vacuo, the residue was taken up in methyl ethyl ketone, and the free base was precipitated as hydrochloride with trimethylsilyl chloride. The yield of Z/E-(2RS)-3-[1-(1-benzyl-2-dimethylaminoethyl)-propenyl]-phenol hydrochloride was 0.09 g (10%).

Example 64

E-(2RS)-[2-benzyl-3-(3-methoxyphenyl)-pent-3-enyl]-dimethyl-amine hydrochloride

The synthesis was carried out up to the fourth stage according to the procedure of Example 48. 5.2 g (14.3 mmole) of E-(2RS)-(3RS)-2-benzyl-1-dimethylamino-3-(3-methoxyphenyl)-pentan-3-ol hydrochloride were then stirred with 7.5 ml of thionyl chloride for 5 hours at 20° C. Excess thionyl chloride was distilled off in vacuo and the residue was taken up in 75 ml of ether. The resultant precipitate was washed with ether. The yield was 4.3 g (78%). 3.6 g (9.4 mmole) of the resultant chloride were hydrogenated with hydrogen at a pressure of 2 bar in the presence of 0.36 g of 10% Pd/C. After filtering off the Pd/C, the substance was precipitated as hydrochloride.

The two stereoisomers Z and E with respect to the double bond are formed as reaction mixture, and were separated by column chromatography (ethylacetate as solvent). The yield of E-(2RS)-[2-benzyl-3-(3-methoxyphenyl)-pent-3-enyl]-dimethyl-amine hydrochloride was 0.79 g (24%).

Example 65

Z-(2RS)-[2-benzyl-3-(3-methoxyphenyl)-pent-3-enyl]-dimethyl-amine hydrochloride

The synthesis was carried out up to the fourth stage according to the procedure of Example 64. The Z isomer was fractionated after precipitating the E isomer. The yield of Z-(2RS)-[2-benzyl-3-(3-methoxyphenyl)-pent-3-enyl]-dimethylamine hydrochloride was 0.4 g (1.1 mmole, 4%) with a melting point of 165° C.

Example 66

(Z/E)-(2RS)-(3RS)-[2-benzyl-3-(3-methoxyphenyl)-pentyl]-dimethylamine hydrochloride The synthesis was carried out according to the procedure of Example 64 for the staring product of the hydrogenation.

3.3 g of the isomer mixture was formed from 10 g (24 mmole) of Z-(2RS)-[2-benzyl-3-(3-methoxyphenyl)-pent-3-enyl]-dimethyl-amine hydrochloride after hydrogenation in the presence of 1.0 g of 10% Pd/C and a hydrogen pressure of 2 bar. The yield was 36% with a melting point of 141.8° C.

Example 67

E-(2RS)-(3RS)-[2-benzyl-3-(3-methoxyphenyl)-pentyl]-dimethylamine hydrochloride

The synthesis was carried out up to the fourth stage according to the procedure of Example 66. E-(2RS)-(3RS)-[2-benzyl-3-(3-methoxyphenyl)-pentyl]-dimethylamine hydrochloride with a melting point of 125° C. was isolated from the isomer mixture by column chromatography separation using ethanol/ethyl acetate 4/1.

Example 68

(2RS)-(3RS)-3-(2-benzyl-3-dimethylamino-1-ethylpropyl)-phenol hydrochloride

The synthesis was carried out according to the procedure of Example 66, followed by a cleavage of the methyl ether with dibutyl aluminium hydride (DIBAlH). To this end 2.8 g (8.0 mmole) of the compound (2RS)-(3RS)-[2-benzyl-3-(3-methoxy-phenyl)-pentyl]-dimethylamine hydrochloride were first of all converted into the free base which was then dissolved in 20 ml of toluene followed by the addition of 25 ml of DIBAlH, and the whole was heated for 3 hours at 110° C. and stirred overnight at 20° C. After working up the reaction mixture (addition of ethanol, water and ethyl acetate), the organic residue was concentrated by evaporation and the residue was taken up in ethyl methyl ketone. After adding sufficient trimethylsilyl chloride to achieve an acidic reaction, 1.3 g, (48%) of (2RS)-(3RS)-3-(2-benzyl-3-dimethylamino-1-ethyl-propyl)-phenol hydrochloride are obtained with a melting point of 166–173° C.

Example 69

(1RS)-(2RS)-2-benzyl-1-(3-methoxyphenyl)-N,N-dimethylpropan-1,3-diamine hydrochloride The synthesis was carried out up to the third stage according to Example 1. 2-benzyl-3-dimethylamino-1-(3-methoxyphenyl)-propan-1-one hydrochloride was then converted with hydroxylamine hydrochloride to the corresponding oxime. For this purpose 5 g (0.015 mole) of 2-benzyl-3-dimethylamino-1-(3-methoxyphenyl)-propan-1-one with 2.1 g (0.03 mole) of hydroxylamine hydrochloride were dissolved in 15 ml of water and 20 ml of ethanol. The reaction time was 5 minutes and the yield of oxime was 1.7 g (33%).

This compound was dried and hydrogenated in ethanol with hydrogen for 48 hours at a pressure of 1 bar in the presence of 1.0 g Pd/c. The yield of (1RS)-(2RS)-2-benzyl-1-(3-methoxyphenyl)-N,N-dimethylpropan-1,3-diamine hydrochloride was 1.1 g (50%); decomposition began at 133° C.

Example 70

(2RS)-2-dimethylamino-2-(3-fluorobenzyl)-1-(3-hydroxyphenyl)-propan-1-one hydrochloride The synthesis was carried out according to the procedure of Example 36. This was then followed by an ether cleavage according to the procedure of Example 68. The compound (2RS)-2-dimethylamino-2-(3-fluorobenzyl)-1-(3-hydroxyphenyl)-propan-1-one hydrochloride was obtained in a total yield of 107 mg (0.5%). The melting point was 153.9° C.

Example 71

(2RS)-2-benzyl-3-dimethylamino-1-(4-methoxy-2,3-dimethylphenyl)-propan-1-one hydrochloride The synthesis was carried out according to the procedure of Example 1. 4-methoxy-2,3-dimethylbenzaldehyde was used instead of 3-methoxybenzaldehyde. The reaction steps involving Grignard reaction, oxidation and Mannich reaction led to the compound (2RS)-2-benzyl-3-dimethylamino-1-(4-methoxy-2,3-dimethylphenyl)-propan-1-one hydrochloride in a total yield of 6.0 g. The melting point is 154.9° C.

Example 72

(2RS)-2-(3-chlorobenzyl)-3-dimethylamino-1-(3-methoxyphenyl)-propan-1-one hydrochloride The synthesis was carried out according to the procedure of Example 1. 1-(2-bromoethyl)-3-chlorobenzene was used instead of 2-phenylethyl bromide. The reaction steps involving Grignard reaction, oxidation and Mannich reaction led to (2RS)-2-(3-chlorobenzyl)-3-dimethylamino-1-(3-methoxyphenyl)-propan-1-one hydrochloride in a total yield of 22 mg. The melting point is 148.7° C.

Example 73

(2RS)-3-dimethylamino-1-(3-methoxyphenyl)-2-(3-methylbenzyl)-propan-1-one hydrochloride The synthesis was carried out according to the procedure of Example 1. 1-(2-bromoethyl)-3-methylbenzene was used instead of 2-phenylethyl bromide. The compound (2RS)-3-dimethylamino-1-(3-methoxyphenyl)-2-(3-methylbenzyl)-propan-1-one hydrochloride was obtained in a total yield of 21 mg. The melting point of the compound is 130.6° C.

Example 74

(2RS)-2-benzyl-3-dimethylamino-1-(2,4,6-trimethylphenyl)-propan-1-one hydrochloride The synthesis was carried out according to the procedure of Example 1. 2,4,6-trimethylbenzaldehyde was used instead of 3-methoxybenzaldehyde. The compound (2RS)-2-benzyl-3-dimethylamino-1-(2,4,6-trimethylphenyl)-propan-1-one hydrochloride was obtained in a total yield of 4.7 g. The melting point of the compound is 165–167° C.

Example 75

(S)-(−)-3-dimethylamino-1-(3-methoxyphenyl)-2-(3-fluorobenzyl)-propan-1-one hydrochloride The synthesis was carried out according to the procedure of Example 36. The racemate was then separated into the two enantiomers by HPLC. A Chirapak AD (10 μm) column is used as the stationary phase and a mixture of hexane:isopropanol:diethylamine (990:10:1) is used as eluent. 22 mg of compound with an angle of rotation of −37.45° are obtained. The melting point range is 154–156° C.

Example 76

(R)-(+)-3-dimethylamino-1-(3-methoxyphenyl)-2-(3-fluorobenzyl)-propan-1-one hydrochloride The synthesis was carried out according to the procedure of Example 36. The racemate was then separated into the two isomers by HPLC. A Chirapak AD (10 μm) column is used as the stationary phase and a mixture of hexane:isopropanol:diethylamine (990:10:1) is used as eluent. 18 mg of compound with an angle of rotation of +37.03° are obtained. The melting point range is 154–156° C.

Example 77

(RS)-3-dimethylamino-1-(3-hydroxyphenyl)-2-(3-methylbenzyl)-propan-1-one hydrochloride The synthesis was carried out according to the procedure of Example 73. The compound is then converted in methanesulfonic acid with methionine into 3-dimethylamino-1-(3-hydroxyphenyl)-2-(3-methylbenzyl)-propan-1-one. The yield was 0.7 g with a melting point of 147° C.

Example 78

(RS)-2-benzyl-1-(2,4-dichlorophenyl)-3-dimethylamino-propan-1-one hydrochloride

The synthesis was carried out according to the procedure of Example 1. 2,4-dichlorobenzaldehyde is used instead of 3-methoxybenzaldehyde. The yield was 2.0 g with a melting point of 122° C.

Example 79

(RS)-3-dimethylamino-2-(4-fluoro-benzyl)-1-(3-hydroxyphenyl)-propan-1-one hydrochloride The synthesis was carried out according to the procedure of Example 37. The compound is then converted in methanesulfonic acid with methionine into (RS)-3-dimethylamino-2-(4-fluoro-benzyl)-1-(3-hydroxyphenyl)-propan-1-one hydrochloride. The yield was 2.1 g with a melting point range of 179–182° C.

Example 80

(RS)-1-(3-methoxyphenyl)-2-methylaminomethyl-3-m-tolylpropan-1-one hydrochloride The synthesis was carried out according to the procedure of Example 73. Methylamine hydrochloride is used instead of dimethylamine hydrochloride in the third stage. The yield of (RS)-1-(3-methoxyphenyl)-2-methylaminomethyl-3-m-tolylpropan-1-one hydrochloride was 0.2 g with a melting point range of 118–120° C.

Example 81

(RS)-2-(3-chlorobenzyl)-3-dimethylamino-1-(3-hydroxyphenyl)-propan-1-one hydrochloride The synthesis was carried out according to Example 72. The compound is then subjected to cleavage with methionine in methanesulfonic acid to form (RS)-2-(3-chlorobenzyl)-3-dimethylamino-1-(3-hydroxyphenyl)-propan-1-one hydrochloride. The yield is 0.75 g with a melting point of 189° C.

Example 82

(RS)-3-(3,4-difluorophenyl)-2-dimethylaminomethyl-1-(3-methoxyphenyl)-propan-1-one hydrochloride The synthesis was carried out according to Example 1. 4-(2-bromoethyl)-3,4-difluorobenzene is used instead of 2-phenylethyl bromide. The yield of (RS)-3-(3,4-difluorophenyl)-2-dimethylaminomethyl-1-(3-methoxyphenyl)-propan-1-one hydrochloride is 0.2 g with a melting point of 128° C.

Example 83

(RS)-3-(3-fluorophenyl)-1-(3-methoxyphenyl)-2-methylamino-methyl-1-propan-1-one hydrochloride The synthesis was carried out according to Example 36. Methylamine hydrochloride is used instead of dimethylamine hydrochloride in the third stage. The yield of (RS)-3-(3-fluorophenyl)-1-(3-methoxyphenyl)-2-methylamino-methyl-1-propan-1-one hydrochloride is 0.5 g with a melting point range of 115–117° C.

Example 84

(RS)-3-(3-fluorophenyl)-1-(3-hydroxyphenyl)-2-methylamino-methyl-propan-1-one hydrochloride The synthesis was carried out according to Example 83. This is then followed by an ether cleavage with methionine in methanesulfonic acid. 0.6 g of (RS)-3-(3-fluorophenyl)-1-(3-hydroxyphenyl)-2-methylaminomethyl-propan-1-one hydrochloride is obtained with a melting point range of 81–85° C.

Example 85

(RS)-1-(2,3-dihydrobenzo[1.4]dioxin-6-yl)-2-dimethylamino-methyl-3-phenylpropan-1-one hydrochloride The synthesis was carried out according to Example 1. 2,3-dihydrobenzo[1,4]dioxine-6-carbaldehyde is used instead of 3-methoxybenzaldehyde in the Grignard reaction. 1.0 g of (RS)-1-(2,3-dihydrobenzo[1,4]dioxin-6-yl)-2-dimethylamino-methyl-3-phenylpropan-1-one hydrochloride is obtained with a melting point of 157° C.

Example 86

(RS)-2-dimethylaminomethyl-1-(3-phenoxyphenyl)-3-phenylpropan-1-one hydrochloride The synthesis was carried out according to Example 1. 3-phenoxybenzaldehyde is used instead of 3-methoxybenzaldehyde in the Grignard reaction. 0.2 g of (RS)-2-dimethylaminomethyl-1-(3-phenoxyphenyl)-3-phenylpropan-1-one hydrochloride is obtained with a melting point of 135° C.

Example 87

(RS)-3-(3,4-difluorophenyl)-2-dimethylaminomethyl-1-(3-hydroxyphenyl)-propan-1-one hydrochloride The synthesis was carried out according to Example 82. The methyl ether is split with methionine in methanesulfonic acid to the phenol. The compound (RS)-3-(3,4-difluorophenyl)-2-dimethylaminomethyl-1-(3-hydroxyphenyl)-propan-1-one hydrochloride is obtained as a brown oil.

Example 88

(RS)-2-dimethylaminomethyl-1-(3-methoxyphenyl)-3-(3-trifluoromethylphenyl)-propan-1-one hydrochloride The synthesis was carried out according to Example 1. 1-(2-bromoethyl)-3-trifluoromethylbenzene is used instead of 2-phenylethyl bromide in the Grignard reaction. 0.3 g of (RS)-2-dimethylaminomethyl-1-(3-methoxyphenyl)-3-(3-trifluoromethylphenyl)-propan-1-one hydrochloride is obtained with a melting point range of 138–146° C.

Example 89

(RS)-2-dimethylaminomethyl-1-(3-hydroxyphenyl)-3-(3-trifluoromethylphenyl)-propan-1-one hydrochloride The synthesis was carried out according to Example 88. This is then followed by an ether cleavage with methionine in methanesulfonic acid to form (RS)-2-dimethylaminomethyl-1-(3-hydroxyphenyl)-3-(3-trifluoromethylphenyl)-propan-1-one hydrochloride with a yield of 0.4 g.

Example 90

Z/E-(2RS)(3RS)-1-(4-chlorophenyl)-3-dimethylaminomethyl-2-(3-methoxyphenyl)-4-phenylbutan-2-ol hydrochloride The synthesis was carried out according to Example 49. 4-chlorobenzyl magnesium chloride is used instead of benzyl magnesium bromide. To this end 4.87 g (30 mmole) of 4-chlorobenzyl magnesium chloride are dissolved in 20 ml of THF and reacted with 0.74 g (30 mmole) of magnesium. The freshly prepared Grignard reagent is reacted with 7.5 g (25 mmole) of 2-benzyl-3-diemethylamino-1-(3-methoxyphenyl)-propan-1-one at 0° C. The yield of Z/E-(2RS)(3RS)-1-(4-chlorophenyl)-3-dimethylaminomethyl-2-(3-methoxyphenyl)-4-phenylbutan-2-ol hydrochloride is 9.5 g (89%).

Example 91

Z/E-(2RS)(3RS)-1-(3-chlorophenyl)-3-dimethylaminomethyl-2-(3-methoxyphenyl)-4-phenylbutan-2-ol hydrochloride The synthesis was carried out according to Example 49. 3-chlorobenzyl magnesium chloride is used instead of benzyl magnesium bromide. To this end 4.87 g (30 mmole) of 3-chlorobenzyl magnesium chloride are dissolved in 20 ml of THF and reacted with 0.74 g (30 mmole) of magnesium. The freshly prepared Grignard reagent is reacted with 7.5 g (25 mmole) of 2-benzyl-3-diemethylamino-1-(3-methoxyphenyl)-propan-1-one at 0° C. The yield of Z/E-(2RS)(3RS)-1-(3-chlorophenyl)-3-dimethylaminomethyl-2-(3-methoxyphenyl)-4-phenylbutan-2-ol hydrochloride after column chromatography separation is 7.0 g (66%).

Example 92

Z/E-(2RS)(3RS)-1-(2-chlorophenyl)-3-dimethylaminomethyl-2-(3-methoxyphenyl)-4-phenylbutan-2-ol hydrochloride The synthesis was carried out according to Example 49. 2-chlorobenzyl magnesium chloride is used instead of benzyl magnesium bromide. To this end 4.87 g (30 mmole) of 2-chlorobenzyl magnesium chloride are dissolved in 20 ml of THF and reacted with 0.74 g (30 mmole) of magnesium. The freshly prepared Grignard reagent is reacted with 7.5 g (25 mmole) of 2-benzyl-3-diemethylamino-1-(3-methoxyphenyl)-propan-1-one at 0° C. The yield of Z/E-(2RS)(3RS)-1-(2-chlorophenyl)-3-dimethylaminomethyl-2-(3-methoxyphenyl)-4-phenylbutan-2-ol hydrochloride after column chromatography separation is 7.6 g (72%).

Pharmacological Investigations

Writing Test in Mice

The analgesic effectiveness of the compounds according to the invention is investigated in mice by the phenylquinone-induced writhing test as modified by I. C. Hendershot, J. Forsaith in J. Pharmacol. Exp. Ther. 125, 237–240 (1959). For this purpose male mice weighing 25–30 g are used. Groups in each case of 10 animals received per substance a dose, 10 minutes after intravenous administration of the test substances, 0.3 ml/mouse of a 0.02% aqueous solution of phenylquinone (phenylbenzoquinone, Sigma, Deisenhofen; solution prepared under the addition of 5% ethanol and storage in a water bath at 45° C.) applied intraperitoneally. The animals were then placed individually in observation cages. The number of pain-induced stretching movements (so-called writhing reactions=straightening of the body with stretching of the rear extremities) was counted with a push-button counter 5–20 minutes after administration of the phenyl quinone. Animals that had only received physiological saline solution with the phenylquinone served as controls.

All substances were tested in a standard dose of 10 mg/kg. The percentage inhibition (% inhibition) of the writhing reactions achieved by a substance was calculated according to the following formula:

$$\% \text{ Inhibition} = 100 - \frac{\text{Writhing reaction of treated animals}}{\text{Writhing reaction of controls}} \times 100$$

All investigated compounds according to the invention exhibited a moderately pronounced to pronounced analgesic effect.

The results of selected writhing investigations are summarised in Table 1.

TABLE 1

Analgesia testing in the writhing test in mice

| Example No. | % Inhibition of Writhing Reactions 10 mg/kg i.v. |
|---|---|
| 2 | 85 |
| 65 | 100 |
| 6 | 84 |
| 7 | 75 |
| 8 | 92 |
| 72 | 85 |
| 11 | 90 |
| 13 | 70 |
| 22 | 62 |
| 26 | 79 |
| 29 | 82 |
| 71 | 94 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A substituted 3-amino-2-benzyl-1-phenylpropane compound of formula I,

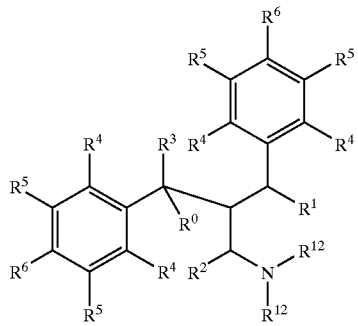

wherein $R^0$ denotes OH or a single bond, $R^1$ denotes H, a $C_{1-10}$-alkyl, an aryl or an aryl radical bound via a $C_{1-6}$-alkylene group $R^2$ denotes H, a $C_{1-10}$-alkyl, an aryl, or an aryl radical bound via a $C_{1-6}$-alkylene group $R^3$ denotes H, OH, $NH_2$, halogen, $OR^7$, $CHR^9$, a $C_{1-10}$-alkyl, a $C_{2-10}$-alkenyl, an aryl or an aryl radical bound via a $C_{1-6}$-alkylene group or together with $R^0$ denote a group =O, =$CHR^{11}$ or =N—OH, $R^4$-radicals, which may be identical or different, denote H, OH, CN, $OR^7$, $SR^7$, halogen, a $C_{1-10}$-alkyl, a $PO(OR^{10})_3$—, an aryl, a heterocyclyl, or an aryl or heterocyclyl radical bound via a $C_{1-6}$-alkylene group, $R^5$-radicals, which may be identical or different, denote H, OH, CN, $OR^7$, $SR^7$, halogen, a $C_{1-10}$-alkyl, a $PO(OR^{10})_3$—, an aryl, a heterocyclyl, or an aryl or heterocyclyl radical bound via a $C_{1-6}$-alkylene group $R^6$-radicals, which may be identical or different, denote H, OH, CN, $OR^7$, $SR^7$, halogen, a $C_{1-10}$-alkyl, a $PO(OR^{10})_3$—, an aryl, a heterocyclyl, or an aryl or heterocyclyl radical bound via a $C_{1-6}$-alkylene group $R^7$-radicals, which may be identical or different, denote a $C_{1-10}$-alkyl, an aryl or an aryl radical bound via a $C_{1-6}$ alkylene group, $R^8$ denotes a $C_{1-10}$-alkyl, an aryl or an aryl radical bound via a $C_{1-6}$-alkylene group, $R^9$ denotes OH, halogen, $OR^{10}$, $SR^{10}$ or a $C_{1-10}$-alkyl radical, $R^{10}$ denotes a $C_{1-10}$-alkyl or a $C_{4-8}$-cycloalkyl radical, $R^{11}$ denotes a $C_{1-10}$-alkyl radical $R^{12}$ radicals, which may be identical or different, denote H, a $C_{1-10}$-alkyl, a $C_{4-8}$-cycloalkyl, an aryl or an aryl radical bound via a $C_{1-6}$-alkylene group, and/or their enantiomers, diastereomers, bases or salts of physiologically compatible acids, the compounds of formula I' being excluded

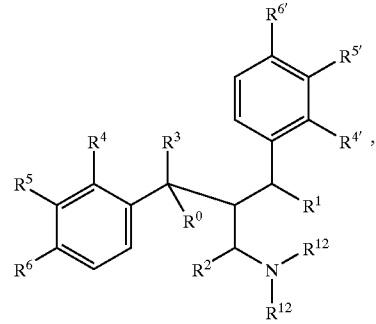

wherein the radicals $R^0$ and $R^3$ together denote the group =O, and $R^1$, $R^2$, $R^4$ to $R^6$ and $R^{4'}$ to $R^{6'}$ denote H, and also the radicals $R^{12}$ in each case denote $CH_3$, as well as the corresponding hydrochloride, wherein $R^0$ and $R^3$ together denote the group =O, $R^6$ denotes the group $OCH_3$ and $R^1$, $R^2$, $R^4$, $R^5$ and $R^{4'}$ to $R^{6'}$ denote H, and also the radicals $R^{12}$ in each case denote $CH_3$, as hydrochloride, wherein $R^0$ and $R^3$ together denote the group =O, $R^{6'}$ denotes the group $OCH_3$ and $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ and $R^3$ together denote the group =O, $R^{6'}$ denotes Cl and $R^1$, $R^2$, $R^4$ to $R^6$, $R^{4'}$ and $R^{5'}$ denote H, and also the radicals $R^{12}$ in each case denote $CH_3$, wherein $R^0$ and $R^3$ together denote the group =O, $R^{5'}$ and $R^{6'}$ in each case denote the group $OCH_3$, and $R^1$, $R^2$, $R^4$ to $R^6$ and $R^{4'}$ denote H, and also the radicals $R^{12}$ in each case denote $CH_3$, as hydrochloride, wherein $R^0$ and $R^3$ together denote the group =O, $R^4$, $R^6$ and $R^{6'}$ in each case denote the group $OCH_3$, and $R^1$, $R^2$, $R^5$, $R^{4'}$ and $R^{5'}$ denote H, and also the radicals $R^{12}$ in each case denote $CH_3$, as hydrochloride, wherein $R^0$ denotes OH, $R^3$ denotes H, $CH_3$, unbranched $C_3H_7$, unbranched $C_5H_{11}$, cyclohexyl, phenyl or benzyl, and $R^1$, $R^2$, $R^4$ to $R^6$ and $R^{4'}$ to $R^{6'}$ denote H, and also the radicals $R^{12}$ in each case denote $CH_3$, as well as the corresponding hydrochlorides, wherein $R^0$ denotes OH, $R^3$ denotes $C_2H_5$ and $R^1$, $R^2$, $R^4$ to $R^6$ and $R^{4'}$ to $R^{6'}$ denote H and also the radicals $R^{12}$ in each case denote $CH_3$, as well as the corresponding hydrochloride and the corresponding methyl iodide, wherein $R^0$ denotes OH, $R^3$ denotes phenyl, $R^6$ denotes Cl, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes Cl, $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ denotes OH, $R^3$ denotes phenyl, $R^{5'}$, $R^{6'}$ in each case denote the group $OCH_3$, $R^1$, $R^2$, $R^4$ to $R^6$ and $R^{4'}$ denote H, and also the radicals $R^{12}$ in each case denote $CH_3$, as hydrochloride, wherein $R^0$ denotes OH, $R^3$ denotes phenyl, $R^6$ denotes the group $OCH_3$, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes the group $OCH_3$, $R^1$, $R^2$, $R^4$ to $R^6$, $R^{4'}$ and $R^{5'}$ denote H, and also the radicals $R^{12}$ in each case denote $CH_3$, as well as the corresponding hydrochloride and the corresponding methyl iodide, wherein $R^0$ denotes OH, $R^3$ denotes phenyl, $R^6$ and $R^{6'}$ in each case denote the group $OCH_3$, $R^1$, $R^2$, $R^4$, $R^5$, $R^{4'}$ and $R^{5'}$ denote H, and also the radicals $R^{12}$ in each case denote $CH_3$, as well as the corresponding hydrochloride, wherein $R^0$ denotes OH, $R^{6'}$ denotes $OCH_3$, $R^1$ to $R^6$, $R^{4'}$ and $R^{5'}$ denote H, and also the radicals $R^{12}$ in each case denote $CH_3$, as well as the corresponding hydrochloride, wherein $R^1$, $R^2$, the radicals $R^4$ to $R^6$, the radicals $R^{4'}$ to $R^{6'}$ in each case denote H, the radicals $R^3$ and $R^0$ together denote the group $=CHR^{11}$, and also the radical $R^{11}$ and in each case the radicals $R^{12}$ denote $CH_3$, as hydrochloride wherein $R^1$, $R^2$, the radicals $R^4$ to $R^6$, the radicals $R^{4'}$ to $R^{6'}$ in each case denote H, the radicals $R^3$ and $R^0$ together denote the group $=N-OH$, and also the radicals $R^{12}$ in each case denote $CH_3$, as well as the corresponding hydrochloride, and wherein $R^1$, $R^2$, the radicals $R^4$ to $R^6$, the radicals $R^{4'}$ to $R^{6'}$ in each case denote H, the radicals $R^3$ and $R^0$ together denote the group $=O$, and also the radicals $R^{12}$ in each case denote $C_2H_5$, as hydrochloride.

2. A compound according to claim 1, wherein $R^1$ is H.
3. A compound according to claim 1, wherein $R^1$ is a $C_{1-3}$-alkyl radical.
4. A compound according to claim 1, wherein $R^1$ is an aryl radical bound via a $C_{1-3}$-alkylene group.
5. A compound according to claim 1, wherein $R^2$ is H.
6. A compound according to claim 1, wherein $R^2$ is a $C_{1-3}$-alkyl radical.
7. A compound according to claim 1, wherein $R^2$ is an aryl radical bound via a $C_{1-3}$-alkylene group.
8. A compound according to claim 1, wherein $R^3$ is H.
9. A compound according to claim 1, wherein $R^3$ is F or Cl.
10. A compound according to claim 1, wherein $R^3$ is a $C_{1-3}$-alkyl radical.
11. A compound according to claim 1, wherein $R^3$ is a $C_{2-3}$-alkenyl radical.
12. A compound according to claim 1, wherein $R^3$ is an aryl radical bound via a $C_{1-3}$-alkylene group.
13. A compound according to claim 1, wherein $R^3$ and $R^0$ together form a $=O$ group.
14. A compound according to claim 1, wherein $R^4$ is H.
15. A compound according to claim 1, wherein $R^4$ is F or Cl.
16. A compound according to claim 1, wherein $R^4$ is a $C_{1-6}$-alkyl radical.
17. A compound according to claim 1, wherein $R^4$ is an aryl or heterocyclyl radical bound via a $C_{1-3}$-alkylene group.
18. A compound according to claim 1, wherein $R^5$ is H.
19. A compound according to claim 1, wherein $R^5$ is F or Cl.
20. A compound according to claim 1, wherein $R^5$ is a $C_{1-6}$-alkyl radical.
21. A compound according to claim 1, wherein $R^5$ is an aryl or heterocyclyl radical bound via a $C_{1-3}$-alkylene group.
22. A compound according to claim 1, wherein $R^6$ is H.
23. A compound according to claim 1, wherein $R^6$ is F or Cl.
24. A compound according to claim 1, wherein $R^6$ is a $C_{1-6}$-alkyl radical.
25. A compound according to claim 1, wherein $R^6$ is an aryl or heterocyclyl radical bound via a $C_{1-3}$-alkylene group.
26. A compound according to claim 1, wherein $R^7$ is a $C_{1-3}$-alkyl radical.
27. A compound according to claim 1, wherein $R^7$ is an aryl radical bound via a $C_{1-3}$-alkylene group.
28. A compound according to claim 1, wherein $R^8$ is a $C_{1-3}$-alkyl radical.
29. A compound according to claim 1, wherein $R^8$ is an aryl radical bound via a $C_{1-3}$-alkylene group.
30. A compound according to claim 1, wherein $R^9$ is F or Cl.
31. A compound according to claim 1, wherein $R^9$ is a $C_{1-3}$-alkyl radical.
32. A compound according to claim 1, wherein $R^{10}$ is a $C_{1-3}$-alkyl radical.
33. A compound according to claim 1, wherein $R^{11}$ is a $C_{1-3}$-alkyl radical.
34. A compound according to claim 1, wherein $R^{12}$ is a $C_{1-3}$-alkyl radical.
35. A compound according to claim 1, selected from the group consisting of:

(Threo)-(2RS)-(3RS)-3-benzyl-4-dimethylamino-2-(3-methoxyphenyl)-butan-2-ol or the corresponding hydrochloride (2RS)-3-[1-(1-benzyl-2-dimethylaminoethyl)-vinyl]-phenol or the corresponding hydrochloride (2RS)-1-(3-benzyloxyphenyl)-2-dimethylaminomethyl-3-phenylpropan-1-one or the corresponding hydrochloride Threo-(2RS)-(3RS)-2-benzyl-1-dimethylamino-3-(3-methoxyphenyl)-pentan-3-ol or the corresponding hydrochloride (3RS)-2-benzyl-1-(4-chlorophenyl)-3-dimethylaminopropan-1-one or the corresponding hydrochloride Threo-(2RS)-(3RS)-2-benzyl-3-(3-benzyloxyphenyl)-1-dimethylaminopentan-3-ol or the corresponding hydrochloride Threo-(2RS)-(3RS)-3-(2-benzyl-3-dimethylamino-1-hydroxypropyl)-phenol or the corresponding hydrochloride Threo-(2RS)-(4RS)-3-benzyl-2-(3-benzyloxyphenyl)-4-dimethylaminobutan-2-ol or the corresponding hydrochloride Threo-(2RS)-(3RS)-3-(2-benzyl-3-dimethylamino-1-methyl-1-hydroxypropyl)-phenol or the corresponding hydrochloride Threo-(2RS)-(3RS)-3-(2-benzyl-3-dimethylamino-1-ethyl-1-hydroxypropyl)-phenol or the corresponding hydrochloride (Erythro/threo)-(2RS)-3-(1-(1-benzyl-2-dimethylaminoethyl)-propenyl]-phenol or the corresponding hydrochloride (2RS)-3-dimethylamino-2-(4-methoxybenzyl)-1-(3-methoxyphenyl)-propan-1-one or the corresponding hydrochloride Erythro-(1RS)-(2RS)-2-benzyl-1-(4-chlorophenyl)-3-dimethylamino-1-(3-methoxyphenyl)-propan-1-ol or the corresponding hydrochloride Threo-(2RS)-(3RS)-2-benzyl-3-(4-chlorophenyl)-1-dimethylaminopentan-3-ol or the corresponding hydrochloride Threo-(2RS)-(3RS)-3-benzyl-2-(4-chlorophenyl)-4-dimethylamino-1-phenylbutan-2-ol or the corresponding hydrochloride Erythro-(2RS)-(3RS)-3-benzyl-2-(4-chlorophenyl)-4-dimethylamino-1-phenylbutan-2-ol or the corresponding hydrochloride Threo-(2RS)-(3RS)-2-benzyl-3-dimethylamino-1,1-bis-(3-methoxyphenyl)-propan-1-ol or the corresponding hydrochloride Threo-(2RS)-(3RS)-2-dimethylaminomethyl-3-(3-methoxyphenyl)-1-phenylhexen-5-ol or the corresponding hydrochloride (2RS)-2-benzyl-3-dimethylamino-1-(3-trifluoromethylphenyl)-propan-1-one or the corresponding hydrochloride (2RS)-2-benzyl-3-dimethylamino-1-(3-hydroxyphenyl)-propan-1-one or the corresponding hydrochloride (2RS)-2-benzyl-1-(3,5-dimethoxyphenyl)-3-dimethylaminopropan-1-one or the corresponding hydrochloride (2RS)-2-benzyl-1-(2,5-dimethoxyphenyl)-3-dimethylaminopropan-1-one or the corresponding hydrochloride (1RS)-(2RS)-2-benzyl-1-(3-methoxyphenyl)-N,N-dimethylpropane-1,3-diamine or the corresponding hydrochloride (2RS)-2-benzyl-1-(2,3-dimethoxyphenyl)-3-dimethylaminopropan-1-one or the corresponding hydrochloride (+)-(R)-2-benzyl-3-dimethylamino-1-(3-methoxyphenyl)-propan-1-one or the corresponding hydrochloride (−)-(S)-2-benzyl-3-dimethylamino-1-(3-methoxyphenyl)-propan-1-one or the corresponding hydrochloride (2RS)-2-benzyl-1-(2,3-dichlorophenyl)-3-dimethylaminopropan-1-one or the corresponding hydrochloride (2RS)-2-benzyl-1-(2,5-dichlorophenyl)-3-dimethylaminopropan-1-one or the corresponding hydrochloride (2RS)-2-benzyl-3-dimethylamino-1-(2,3,4-trimethoxyphenyl)-propan-1-one or the corresponding hydrochloride (2RS)-2-benzyl-3-dimethylamino-1-(3,4,5-trimethoxyphenyl)-propan-1-one or the corresponding hydrochloride Erythro-(2RS)-[2-benzyl-3-(3-methoxyphenyl)-pent-3-enyl]-dimethylamine or the corresponding hydrochloride (2RS)-2-benzyl-1-(2,5-dihydroxyphenyl)-3-dimethylaminopropan-1-one or the corresponding hydrochloride Threo-(2RS)-(3RS)-2-dimethylaminomethyl-3-(3-methoxyphenyl)-1,3-diphenylpropan-1-one or the corresponding hydrochloride (2RS)-2-benzyl-3-dimethylamino-1-(2-methoxyphenyl)-propan-1-one or the corresponding hydrochloride (2RS)-2-benzyl-3-dimethylamino-1-naphthalen-2-yl-propan-1-one or the corresponding hydrochloride (2RS)-2-benzyl-3-dimethylamino-1-phenanthren-3-yl-propan-1-one or the corresponding hydrochloride (2RS)-2-benzyl-3-dimethylamino-1-(2-hydroxyphenyl)-propan-1-one or the corresponding hydrochloride (2RS)-2-benzyl-3-dimethylamino-1-(2-fluorophenyl)-propan-1-one or the corresponding hydrochloride (2RS)-2-benzyl-3-dimethylamino-1-(3-methylsulfanylphenyl)-propan-1-one or the corresponding hydrochloride Threo-(2RS)-(3RS)-[2-benzyl-3-(3-methoxyphenyl)-pentyl]-dimethylamine or the corresponding hydrochloride (Erythro/threo)-(2RS)-(3RS)-[2-benzyl-3-(3-methoxyphenyl)-pentyl]-dimethylamine or the corresponding hydrochloride (2RS)-2-benzyl-3-dimethylamino-1-(2-hydroxy-5-methoxyphenyl)-propan-1-one or the corresponding hydrochloride (2RS)-3-(2-benzyl-3-dimethylaminopropionyl)-benzonitrile or the corresponding hydrochloride (2RS)-(3RS)-2-dimethylaminomethyl-1,3,3-tris-(3-methoxyphenyl)-propan-1-one or the corresponding hydrochloride (2RS)-2-benzyl-1-biphenyl-3-yl-3-dimethylaminopropan-1-one or the corresponding hydrochloride (2RS)-2-benzyl-3-dimethylamino-1-(6-methoxynaphthalen-2-yl)-propan-1-one or the corresponding hydrochloride (2RS)-(3RS)-2-dimethylaminomethyl-1,3-bis-(3-methoxyphenyl)-3-phenylpropan-1-one or the corresponding hydrochloride Erythro-(2RS)-(3RS)-2-dimethylaminomethyl-1-(3-methoxyphenyl)-3,4-diphenylbutan-1-one or the corresponding hydrochloride (2RS)-2-benzyl-3-dimethylamino-1-(6-hydroxynaphthalen-2-yl)-propan-1-one or the corresponding hydrochloride (2RS)-(3RS)-3-(2-benzyl-3-dimethylamino-1-ethylpropyl)-phenol or the corresponding hydrochloride (2RS)-2-benzyl-1-biphenyl-2-yl-3-dimethylaminopropan-1-one or the corresponding hydrochloride (2RS)-(3RS)-2-dimethylaminomethyl-1-(3-methoxyphenyl)-3-phenylpentan-1-one or the corresponding hydrochloride (2RS)-2-benzyl-1-(2-chloro-4-fluorophenyl)-3-dimethylaminopropan-1-one or the corresponding hydrochloride (2RS)-2-dimethylaminomethyl-1-[(1RS)-3-(1-hydroxy-3-phenylpropyl)-phenyl]-3-phenylpropan-1-one or the corresponding hydrochloride (2RS)-3-dimethylamino-2-(2-fluorobenzyl)-1-(3-methoxyphenyl)-propan-1-one or the corresponding hydrochloride (2RS)-3-dimethylamino-2-(3-fluorobenzyl)-1-(3-methoxyphenyl)-propan-1-one or the corresponding hydrochloride (2RS)-3-dimethylamino-2-(4-fluorobenzyl)-1-(3-methoxyphenyl)-propan-1-one or the corresponding hydrochloride (2RS)-(3RS)-2-dimethylaminomethyl-3,3-bis-(3-methoxyphenyl)-1-naphthalen-2-yl-propan-1-one or the corresponding hydrochloride (2RS)-2-benzyl-3-dimethylamino-1-(3-methoxyphenyl)-propan-1-one or the corresponding hydrochloride Erythro-(2RS)-(3RS)-2-dimethylaminomethyl-1,3-diphenylpentan-1-one or the corresponding hydrochloride (2RS)-(3RS)-2-dimethylaminomethyl-1,3-diphenyl-3-p-tolylpropan-1-one or the corresponding hydrochloride (2RS)-(3RS)-2-dimethylaminomethyl-1,3,6-triphenylhexan-1-one or the corresponding hydrochloride Threo-(2RS)-(3RS)-3-benzyl-4-dimethylamino-2-(3-methoxyphenyl)-1-phenylbutan-2-ol or the corresponding hydrochloride (2RS)-(3RS)-3-benzyl-4-dimethylamino-1,1,1-trifluoro-2-(3-methoxyphenyl)-butan-2-ol Threo-(2RS)-[2-benzyl-3-(3-methoxyphenyl)-pent-3-enyl]-dimethylamine or the corresponding hydrochloride (+)-(R)-2-benzyl-3-dimethylamino-1-(3-hydroxyphenyl)-propan-1-one or the corresponding hydrochloride (2RS)-3-dimethylamino-2-(3-methylbenzyl)-1-(3-methoxyphenyl)-propan-1-one or the corresponding hydrochloride (−)-(S)-2-benzyl-3-dimethylamino-1-(3-hydroxyphenyl)-propan-1-one or the corresponding hydrochloride (2RS)-2-dimethylamino-2-(3-fluorobenzyl)-1-(3-hydroxyphenyl)-propan-1-one or the corresponding hydrochloride (2RS)-3-dimethylamino-2-(3-methoxybenzyl)-1-(3-methoxyphenyl)-propan-1-one or the corresponding hydrochloride (2RS)-2-benzyl-3-dimethylamino-1-(4-methoxy-2,3-dimethylphenyl)-propan-1-one or the corresponding hydrochloride (2RS)-2-(3-chlorobenzyl)-3-dimethylamino-1-(3-methoxyphenyl)-propan-1-one or the corresponding hydrochloride (2RS)-3-dimethylamino-1-(3-methoxyphenyl)-2-(3-methylbenzyl)-propan-1-one or the corresponding hydrochloride (2RS)-2-benzyl-3-dimethylamino-1-(2,4,6-trimethylphenyl)-propan-1-one or the corresponding hydrochloride (S)-(−)-3-dimethylamino-1-(3-methoxyphenyl)-2-(3-fluorobenzyl)-propan-1-one or the corresponding hydrochloride (R)-(+)-3-dimethylamino-1-(3-methoxyphenyl)-2-(3-fluorobenzyl)-propan-1-one or the corresponding hydrochloride (RS)-3-dimethylamino-1-(3-hydroxyphenyl)-2-(3-methylbenzyl)-propan-1-one or the corresponding hydrochloride (RS)-2-benzyl-1-(2,4-dichlorophenyl)-3-dimethylaminopropan-1-one or the corresponding hydrochloride (RS)-3-dimethylamino-2-(4-flurobenzyl)-1-(3-hydroxyphenyl)-propan-1-one or the corresponding hydrochloride (RS)-1-(3-methoxyphenyl)-2-methylaminomethyl-3-m-tolylpropan-1-one or the corresponding hydrochloride (RS)-2-(3-chlorobenzyl)-3-dimethylamino-1-(3-hydroxyphenyl)-propan-1-one or the corresponding hydrochloride (RS)-3-(3,4-difluorophenyl)-2-dimethylaminomethyl-1-(3-methoxyphenyl)-propan-1-one or the corresponding hydrochloride (RS)-3-(3-fluorophenyl)-1-(3-methoxyphenyl)-2-methylaminomethyl-1-propan-1-one or the corresponding hydrochloride (RS)-3-(3-fluorophenyl)-1-(3-hydroxyphenyl)-2-methylaminomethylpropan-1-one or the corresponding hydrochloride (RS)-1-(2,3-dihydrobenzo[1,4]dioxin-6-yl)-2-dimethylaminomethyl-3-phenylpropan-1-one or the corresponding hydrochloride (RS)-2-dimethylaminomethyl-1-(3-phenoxyphenyl)-3-phenylpropan-1-one or the corresponding hydrochloride (RS)-3-(3,4-difluorophenyl)-2-dimethylaminomethyl-1-(3-hydroxyphenyl)-propan-1-one or the corresponding hydrochloride (RS)-2-dimethylaminomethyl-1-(3-methoxyphenyl)-3-(3-trifluoromethylphenyl)propan-1-one or the corresponding hydrochloride (RS)-2-dimethylaminomethyl-1-(3-hydroxyphenyl)-3-(3-trifluoromethylphenyl)propan-1-one or the corresponding hydrochloride Erythro/threo-(2RS)(3RS)-1-(4-chlorophenyl)-3-dimethylaminomethyl-2-(3-methoxyphenyl)-4-phenylbutan-2-ol or the corresponding hydrochloride Erythro/threo-(2RS)(3RS)-1-(3-chlorophenyl)-3-dimethylaminomethyl-2-(3-methoxyphenyl)-4-phenylbutan-2-ol or the corresponding hydrochloride and Erythro/threo-(2RS)(3RS)-1-(2-chlorophenyl)-3-dimethylaminomethyl-2-(3-methoxyphenyl)-4-phenylbutan-2-ol or the corresponding hydrochloride.

36. A process for preparing a substituted 3-amino-2-benzyl-1-phenylpropane compound of formula I according to claim 1, in which $R^0$ and $R^3$ together form a =O group and $R^1$ is H, said process comprising reacting a substituted aldehyde of formula II

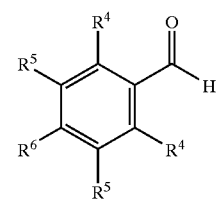

with a compound of formula III, wherein X is Br, Cl or I

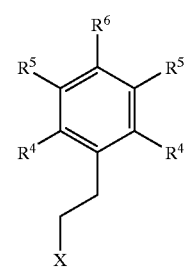

in the presence of magnesium in a Grignard reaction to form a compound of formula IV

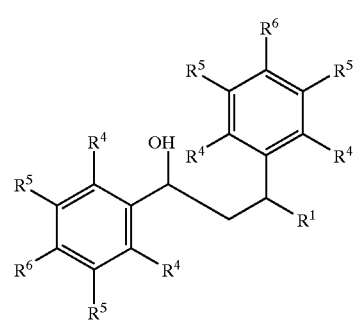

isolating and purifying the compound of formula IV, thereafter oxidizing the compound of formula IV in solution with an oxidizing agent to give a compound of formula V

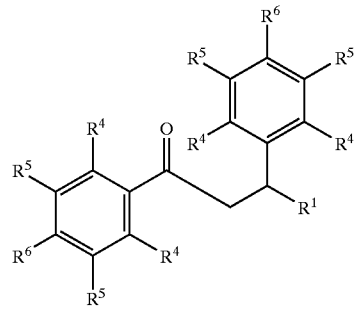

reacting the compound of formula V with an iminium salt of an aldehyde and a compound of formula $NH(R^{12})_2 \cdot HCl$ wherein $R^{12}$ has the meaning according to claim 1, in a Mannich reaction to give a compound of formula VI

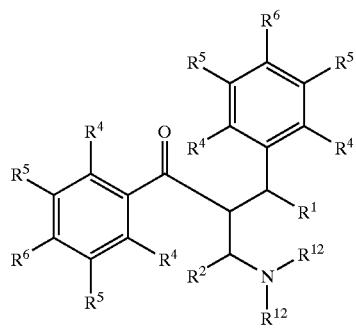

and isolating the compound of formula VI.

37. A process according to claim 36, wherein X in the compound of formula III is Br.

38. A process according to claim 36, wherein the compound of formula IV is oxidized in an aqueous or ethereal solution.

39. A process according to claim 36, wherein the compound of formula IV is oxidized with an inorganic oxidizing agent selected from the group consisting of potassium dichromate and sodium hypochlorite.

40. A process according to claim 36, for preparing a substituted 3-amino-2-benzyl-1-phenylpropane compound of formula I, wherein $R^0$ is OH, and $R^1$ is H, said process comprising reacting a compound of formula VI with an organometallic compound of formula $R^3MX$, wherein M is Li, Mg or Zn, and X is Cl, Br or I, to form a compound of formula VII

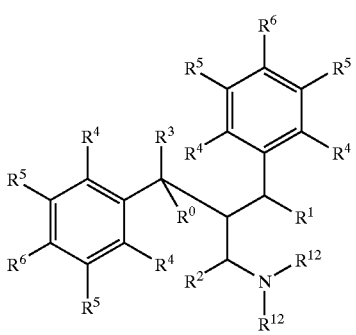

and isolating and purifying the compound of formula VII.

41. A process according to claim 40, for preparing a substituted 3-amino-2-benzyl-1-phenylpropane compound of formula I wherein $R^0$ and $R^3$ together form a =$CHR^{11}$ group, and $R^1$ is H, said process comprising treating a compound of formula VII with hydrogen bromide to form an olefin of formula VIII

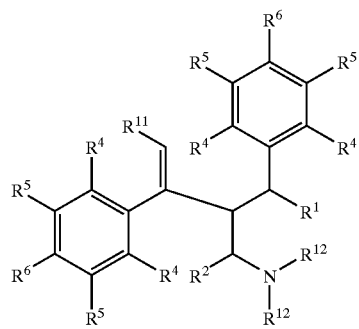

and isolating the olefin of Formula VIII.

42. A process for preparing a substituted 3-amino-2-benzyl-1-phenylpropane compound of formula I according to claim 1, wherein $R^0$ and $R^3$ together form an =O group, and $R^1$ is other than H, said process comprising reacting a substituted acetaldehyde of formula X

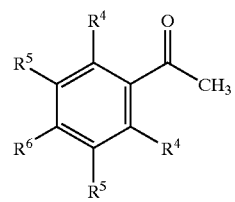

with a substituted benzaldehyde of formula XI

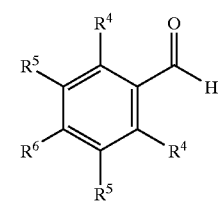

in an aldol condensation to form a substituted 1,3-diphenylpropenone of formula XII

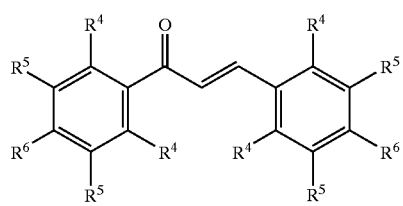

isolating and purifying the compound of formula XII,
  thereafter reacting the compound of formula XII with a compound converted from a compound of formula $R^1Br$ with magnesium into a Grignard compound and by a transmetallation with copper (I) iodide into the corresponding cuprates, to form an enolate,
  reacting the enolate in situ with an iminium salt of an aldehyde and a compound of the formula $NH(R^{12})_2$.

HCl, wherein $R^{12}$ has the meaning according to claim 1, to obtain a compound of formula XIII

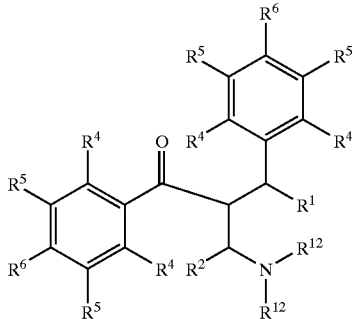

and thereafter isolating and purifying the compound of formula XIII.

43. A process according to claim 42, for preparing a substituted 3-amino-2-benzyl-3-dimethylamino-1-phenylpropane compound of formula I wherein $R^0$ is OH, and $R^1$ is other than H, said process comprising reacting a compound of formula XIII with a compound of the formula $R^3MX$, wherein M is Li, Mg or Zn, and X is Cl, Br or I, to obtain a compound of formula XIV

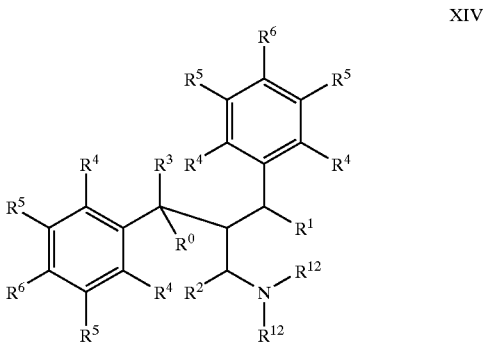

and isolating and purifying the compound of formula XIV.

44. A process according to claim 43, for preparing a substituted 3-amino-2-benzyl-1-phenylpropane compound of formula I, wherein $R^0$ and $R^3$ together form a $=CHR^{11}$ group and $R^1$ is other than H, said process comprising treating a compound of formula XIV with hydrogen bromide to obtain an olefin of formula XV

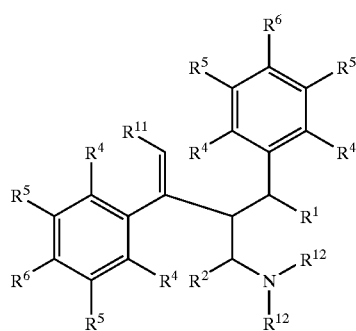

and isolating and purifying the olefin of formula XV.

45. A process for preparing a compound of formula I, wherein $R^4$ and/or $R^5$ and/or $R^6$ denote an OH group and $R^0$ to $R^3$ as well as $R^{12}$ have the meanings specified in claim 1, said process comprising treating a compound of formula I in which $R^4$ and/or $R^5$ and/or $R^6$ denote a methoxy group and $R^0$ to $R^3$ as well as $R^{12}$ have the meanings specified in claim 1, with methionine in methanesulfonic acid at a temperature $\geq 60°$ C.

46. A pharmaceutical composition comprising at least one pharmaceutical carrier, auxiliary substance or adjuvant and at least one compound of formula I according to claim 1 or an enantiomer, diastereomer, or physiologically compatible salt thereof, with the exception of the compounds of formula I' according to claim 1, wherein the radicals $R^0$ and $R^3$ together denote the group $=O$ and $R^1$, $R^2$, $R^4$ to $R^6$ and $R^{4'}$ to $R^{6'}$ denote H and also the radicals $R^{12}$ in each case denote $CH_3$, as well as the corresponding hydrochloride, wherein $R^0$ and $R^3$ together denote the group $=O$, $R^6$ denotes the group $OCH_3$ and $R^1$, $R^2$, $R^4$, $R^5$ and $R^{4'}$ to $R^{6'}$ denote H, and also the radicals $R^{12}$ in each case denote $CH_3$, as hydrochloride, wherein $R^0$ and $R^3$ together denote the group $=O$, $R^{6'}$ denotes the group $OCH_3$ and $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ and $R^3$ together denote the group $=O$, $R^{6'}$ denotes Cl and $R^1$, $R^2$, $R^4$ to $R^6$, $R^{4'}$ and $R^{5'}$ denote H, and also the radicals $R^{12}$ in each case denote $CH_3$, wherein $R^0$ and $R^3$ together denote the group $=O$, $R^{5'}$ and $R^{6'}$ in each case denote the group $OCH_3$, and $R^1$, $R^2$, $R^4$ to $R^6$ and $R^{4'}$ denote H, and also the radicals $R^{12}$ in each case denote $CH_3$, as hydrochloride, wherein $R^0$ and $R^3$ together denote the group $=O$, $R^4$, $R^6$ and $R^{6'}$ in each case denote the group $OCH_3$, and $R^1$, $R^2$, $R^5$, $R^{4'}$ and $R^{5'}$ denote H, and also the radicals $R^{12}$ in each case denote $CH_3$, as hydrochloride, wherein $R^0$ denotes OH, $R^3$ denotes H, $CH_3$, unbranched $C_3H_7$, unbranched $C_5H_{11}$, cyclohexyl, phenyl or benzyl, and $R^1$, $R^2$, $R^4$ to $R^6$ and $R^{4'}$ to $R^{6'}$ denote H, and also the radicals $R^{12}$ in each case denote $CH_3$, as well as the corresponding hydrochlorides, wherein $R^0$ denotes OH, $R^3$ denotes $C_2H_5$ and $R^1$, $R^2$, $R^4$ to $R^6$ and $R^{4'}$ to $R^{6'}$ denote H and also the radicals $R^{12}$ in each case denote $CH_3$, as well as the corresponding hydrochloride and the corresponding methyl iodide, wherein $R^0$ denotes OH, $R^3$ denotes phenyl, $R^6$ denotes Cl, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes Cl, $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ denotes OH, $R^3$ denotes phenyl, $R^{5'}$, $R^{6'}$ in each case denote the group $OCH_3$, $R^1$, $R^2$, $R^4$ to $R^6$ and $R^{4'}$ denote H, and also the radicals $R^{12}$ in each case denote $CH_3$, as hydrochloride, wherein $R^0$ denotes OH, $R^3$ denotes phenyl, $R^6$ denotes the group $OCH_3$, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes the group $OCH_3$, $R^1$, $R^2$, $R^4$ to $R^6$, $R^{4'}$ and $R^{5'}$ denote H, and also the radicals $R^{12}$ in each case denote $CH_3$, as well as the corresponding hydrochloride and the corresponding methyl iodide, wherein $R^0$ denotes OH, $R^3$ denotes phenyl, $R^6$ and $R^{6'}$ in each case denote the group $OCH_3$, $R^1$, $R^2$, $R^4$, $R^5$, $R^{4'}$ and $R^{5'}$ denote H, and also the radicals $R^{12}$ in each case denote $CH_3$, as well as the corresponding hydrochloride, wherein $R^0$ denotes OH, $R^{6'}$ denotes $OCH_3$, $R^1$ to $R^6$, $R^{4'}$ $R^{5'}$ denote H, and also the radicals $R^{12}$ in each case denote $CH_3$, as well as the corresponding hydrochloride, wherein $R^1$, $R^2$, the radicals $R^4$ to $R^6$, the radicals $R^{4'}$ to $R^{6'}$ in each case denote H, the radicals $R^3$ and $R^0$ together denote the group $=CHR^{11}$, and also the radical $R^{11}$ and in each case the radicals $R^{12}$ denote $CH_3$, as hydrochloride and wherein $R^1$, $R^2$, the radicals $R^4$ to $R^6$, the radicals $R^{4'}$ to $R^{6'}$ in each case denote H, the radicals $R^3$ and $R^0$ together denote the group $=N-OH$, and also the radicals $R^{12}$ in each case denote $CH_3$, as well as the corresponding hydrochloride.

47. A method of treating pain comprising administering to a patient suffering from pain an effective amount of a pharmaceutical composition according to claim 46.

48. A method of treating urinary incontinence comprising administering to a patient suffering from urinary incontinence an effective amount of a pharmaceutical composition according to claim 46.

49. A method of treating pain comprising administering to a patient suffering from pain an effective amount of at least one compound of formula I according to claim 1 or an enantiomer, diastereomer, or physiologically compatible salt thereof, with the exception of the compounds of formula I' according to claim 1 wherein the radicals $R^0$ and $R^3$ together denote the group $=O$ and $R^1$, $R^2$, $R^4$ to $R^6$ and $R^{4'}$ to $R^{6'}$ denote H and also the radicals $R^{12}$ in each case denote $CH_3$, as well as the corresponding hydrochloride, wherein $R^0$ and $R^3$ together denote the group $=O$, $R^6$ denotes the group $OCH_3$ and $R^1$, $R^2$, $R^4$, $R^5$ and $R^{4'}$ to $R^{6'}$ denote H, and also the radicals $R^{12}$ in each case denote $CH_3$, as hydrochloride, wherein $R^0$ and $R^3$ together denote the group $=O$, $R^{6'}$ denotes the group $OCH_3$ and $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ and $R^3$ together denote the group $=O$, $R^{6'}$ denotes Cl and $R^1$, $R^2$, $R^4$ to $R^6$, $R^{4'}$ and $R^{5'}$ denote H, and also the radicals $R^{12}$ in each case denote $CH_3$, wherein $R^0$ and $R^3$ together denote the group $=O$, $R^{5'}$ and $R^{6'}$ in each case denote the group $OCH_3$, and $R^1$, $R^2$, $R^4$ to $R^6$ and $R^{4'}$ denote H, and also the radicals $R^{12}$ in each case denote $CH_3$, as hydrochloride, wherein $R^0$ and $R^3$ together denote the group $=O$, $R^4$, $R^6$ and $R^{6'}$ in each case denote the group $OCH_3$, and $R^1$, $R^2$, $R^5$, $R^{4'}$ and $R^{5'}$ denote H, and also the radicals $R^{12}$ in each case denote $CH_3$, as hydrochloride, wherein $R^0$ denotes OH, $R^3$ denotes H, $CH_3$, unbranched $C_3H_7$, unbranched $C_5H_{11}$, cyclohexyl, phenyl or benzyl, and $R^1$, $R^2$, $R^4$ to $R^6$ and $R^{4'}$ to $R^{6'}$ denote H, and also the radicals $R^{12}$ in each case denote $CH_3$, as well as the corresponding hydrochlorides, wherein $R^0$ denotes OH, $R^3$ denotes $C_2H_5$ and $R^1$, $R^2$, $R^4$ to $R^6$ and $R^{4'}$ to $R^{6'}$ denote H and also the radicals $R^{12}$ in each case denote $CH_3$, as well as the corresponding hydrochloride and the corresponding methyl iodide, wherein $R^0$ denotes OH, $R^3$ denotes phenyl, $R^6$ denotes Cl, $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes Cl and $R^1$, $R^2$, $R^4$ to $R^6$, $R^{4'}$ and $R^{5'}$ denote H, and also the radicals $R^{12}$ in each case denote $CH_3$, as well as the corresponding hydrochloride, wherein $R^0$ denotes OH, $R^3$ denotes phenyl, $R^{5'}$, $R^{6'}$ in each case denote the group $OCH_3$ and $R^1$, $R^2$, $R^4$ to $R^6$ and $R^{4'}$ denote H, and also the radicals $R^{12}$ in each case denote $CH_3$, as hydrochloride, wherein $R^0$ denotes OH, $R^3$ denotes phenyl, $R^6$ denotes the group $OCH_3$ and $R^1$, $R^2$, $R^4$, $R^5$ and $R^{4'}$ to $R^{6'}$ denote H, and also the radicals $R^{12}$ in each case denote $CH_3$, as well as the corresponding hydrochloride, wherein $R^0$ denotes OH, $R^3$ denotes phenyl, $R^{6'}$ denotes the group $OCH_3$ and $R^1$, $R^2$, $R^4$ to $R^6$, $R^{4'}$ and $R^{5'}$ denote H, and also the radicals $R^{12}$ in each case denote $CH_3$, as well as the corresponding hydrochloride and the corresponding methyl iodide, wherein $R^0$ denotes OH, $R^3$ denotes phenyl, $R^6$ and $R^{6'}$ in each case denote the group $OCH_3$ and $R^1$, $R^2$, $R^4$, $R^5$, $R^{4'}$ and $R^{5'}$ denote H, and also the radicals $R^{12}$ in each case denote $CH_3$, as well as the corresponding hydrochloride, wherein $R^0$ denotes OH, $R^{6'}$ denotes $OCH_3$, $R^1$ to $R^6$, $R^{4'}$ and $R^{5'}$ denote H, and also the radicals $R^{12}$ in each case denote $CH_3$, as well as the corresponding hydrochloride, and wherein $R^1$, $R^2$, the radicals $R^4$ to $R^6$, the radicals $R^{4'}$ to $R^{6'}$ in each case denote H, the radicals $R^3$ and $R^0$ together denote the group $=CHR^{11}$, and also the radical $R^{11}$ and in each case the radicals $R^{12}$ denote $CH_3$, as hydrochloride.

50. A method of treating urinary incontinence comprising administering to a patient suffering from urinary incontinence an effective amount of at least one compound of formula I according to claim 1 or an enantiomer, diastereomer, or physiologically compatible salt thereof.

51. A method of treating inflammation comprising administering to a patient suffering from inflammation an effective amount of at least one compound of formula I according to claim 1 or an enantiomer, diastereomer, or physiologically compatible salt thereof.

52. A method of treating an allergy comprising administering to a patient suffering from an allergy an effective amount of at least one compound of formula I according to claim 1 or an enantiomer, diastereomer, or physiologically compatible salt thereof.

53. A method of treating depression comprising administering to a patient suffering from depression an effective amount of at least one compound of formula I according to claim 1 or an enantiomer, diastereomer, or physiologically compatible salt thereof.

54. A method of treating drug or alcohol misuse comprising administering to a patient suffering from drug or alcohol misuse an effective amount of at least one compound of formula I according to claim 1 or an enantiomer, diastereomer, or physiologically compatible salt thereof.

55. A method of treating gastritis comprising administering to a patient suffering from gastritis an effective amount of at least one compound of formula I according to claim 1 or an enantiomer, diastereomer, or physiologically compatible salt thereof.

56. A method of treating diarrhea comprising administering to a patient suffering from diarrhea an effective amount of at least one compound of formula I according to claim 1 or an enantiomer, diastereomer, or physiologically compatible salt thereof.

57. A method of treating a cardiovascular disorder comprising administering to a patient suffering from a cardiovascular disorder an effective amount of at least one compound of formula I according to claim 1 or an enantiomer, diastereomer, or physiologically compatible salt thereof.

58. A method of treating a respiratory condition comprising administering to a patient suffering from a respiratory condition an effective amount of at least one compound of formula I according to claim 1 or an enantiomer, diastereomer, or physiologically compatible salt thereof.

59. A method of treating a cough comprising administering to a patient suffering from coughs an effective amount of at least one compound of formula I according to claim 1 or an enantiomer, diastereomer, or physiologically compatible salt thereof.

60. A method of treating a psychiatric disorder comprising administering to a patient suffering from a psychiatric disorder an effective amount of at least one compound of formula I according to claim 1 or an enantiomer, diastereomer, or physiologically compatible salt thereof.

61. A method of treating epilepsy comprising administering to a patient suffering from epilepsy an effective amount of at least one compound of formula I according to claim 1 or an enantiomer, diastereomer, or physiologically compatible salt thereof.

* * * * *